United States Patent
King et al.

(10) Patent No.: US 8,353,968 B2
(45) Date of Patent: Jan. 15, 2013

(54) SPRING ORTHOTIC DEVICE

(75) Inventors: Steven August King, Kihei, HI (US);
Paul Hewitt, Sacramento, CA (US)

(73) Assignee: King Family Kingetics, LLC, Kihei, HI (US)

( * ) Notice: Subject to any disclaimer, the term of this patent is extended or adjusted under 35 U.S.C. 154(b) by 0 days.

(21) Appl. No.: 12/919,320

(22) PCT Filed: Feb. 8, 2010

(86) PCT No.: PCT/US2010/023527
§ 371 (c)(1),
(2), (4) Date: Aug. 25, 2010

(87) PCT Pub. No.: WO2010/091377
PCT Pub. Date: Aug. 12, 2010

(65) Prior Publication Data
US 2011/0009982 A1 Jan. 13, 2011

Related U.S. Application Data

(60) Provisional application No. 61/150,789, filed on Feb. 8, 2009.

(51) Int. Cl.
*A61F 2/66* (2006.01)
*A43B 13/28* (2006.01)
(52) U.S. Cl. .................... 623/55; 36/27; 36/38
(58) Field of Classification Search ............... 36/27, 38; 623/55; 602/65
See application file for complete search history.

(56) References Cited

U.S. PATENT DOCUMENTS

| | | |
|---|---|---|
| 1,958,097 A | 5/1934 | Shaw |
| 4,510,700 A | 4/1985 | Brown |
| 4,638,575 A | 1/1987 | Illustrato |
| 4,821,432 A | 4/1989 | Reiber |
| 4,858,338 A | 8/1989 | Schmid |
| D305,954 S | 2/1990 | Kin |
| 5,179,791 A | 1/1993 | Lain |
| 5,203,095 A | 4/1993 | Allen |
| 5,528,842 A | 6/1996 | Ricci et al. |
| 5,897,515 A | 4/1999 | Willner et al. |
| 6,029,374 A | 2/2000 | Herr et al. |
| 6,098,319 A | 8/2000 | Epstein |
| 6,345,455 B1 | 2/2002 | Greer, Jr. et al. |
| 6,349,487 B1 | 2/2002 | Hice |

(Continued)

FOREIGN PATENT DOCUMENTS

EP 0992199 B1 10/2005

(Continued)

OTHER PUBLICATIONS

Patent Cooperation Treaty International Searching Authority, International Patent Application No. PCT/US2010/023527, International Search Report and Written Opinion dated Dec. 6, 2010.

(Continued)

*Primary Examiner* — Bruce E Snow
(74) *Attorney, Agent, or Firm* — Michael Fedrick; Loza & Loza, LLP

(57) ABSTRACT

A spring orthotic device comprising a cradle for contacting the foot of a user, a spring plate underneath the cradle, a ventral pivot beneath the spring plate, and a dorsal pivot above the spring plate and below the cradle located proximally of the ventral pivot.

21 Claims, 21 Drawing Sheets

U.S. PATENT DOCUMENTS

| | | |
|---|---|---|
| 6,598,319 B2 | 7/2003 | Hardt |
| 6,745,501 B2 | 6/2004 | Brown |
| D497,474 S | 10/2004 | Sanchez |
| 6,874,258 B2 | 4/2005 | Clough et al. |
| 6,887,213 B2 | 5/2005 | Smits |
| 7,062,865 B1 | 6/2006 | Nordt, III |
| 7,100,308 B2 * | 9/2006 | Aveni ................................ 36/27 |
| 7,124,518 B1 | 10/2006 | Brown |
| 7,266,910 B2 | 9/2007 | Ingimundarson |
| 2006/0174515 A1 | 8/2006 | Wilkinson |
| 2008/0060229 A1 | 3/2008 | Epstein |

FOREIGN PATENT DOCUMENTS

| | | |
|---|---|---|
| JP | 10-257904 A | 9/1998 |
| JP | 2001-112505 A | 4/2001 |
| KR | 10-1999-0068600 A | 9/1999 |
| KR | 2007078764 | 8/2007 |
| WO | 2006068513 | 6/2006 |

OTHER PUBLICATIONS

MyFootShop website, Spring Plate—Carbon/Graphite Fiber Insert, Jan. 19, 2009.

* cited by examiner

SPRING ORTHOTIC DEVICE

BACKGROUND

Generally, shoes consist of an insole, i.e. the interior bottom of a shoe, an outsole which contacts the ground, and in some cases a midsole between the outsole and the insole. The purpose of a midsole is often to act as a shock absorber to absorb the impact of walking and provide extra cushion, and for this reason materials such as EVA and polyurethane are often used.

Orthotic inserts, also called arch supports, are inserts placed into a shoe either on top of or in place of the insole. Orthotics are used to correct foot alignment and side-to-side movement during walking and thereby decrease pain, not only in the foot, but also in other parts of the body such as the knee, hip and lower back. They can also increase stability in an unstable joint and prevent a deformed foot from developing additional problems. Rigid orthotic devices are generally made by casting a mold, and can be made from materials such as plastic or carbon fiber.

Carbon fiber and steel plates inserted into a shoe are also known for use in stiffening the sole of the shoe. Such inserts can provide additional comfort for individuals with arthritis.

SUMMARY

The use of hard surfaces (stone, concrete, and asphalt) in modern human environments has changed the forces encountered by the human musculoskeletal system as compared to the forces which it evolved to sustain. Impact energies from such surfaces enter the body through compression/longitudinal waves, higher frequency and shorter length waves through boney and dense tissues, and lower frequency and longer length waves through soft and fatty tissues. Such impact energy is then converted into breaking power, potential energy of muscles and tendons, heat, and sometimes physical damage leading to injury. The increase in body weight and general decrease in exercise and fitness experienced by some individuals can exacerbate such physical damage.

The present invention provides a means to alleviate the physical damage and injury experienced by a subject due to impact with the ground. The present device comprises a simple spring machine tricorrectional joint/spring orthotic that produces a mechanical advantage which is used to enhance the efficiency and stability of gait for both able and less mobile individuals while providing protection from puncture wounds.

SUMMARY

The present device is useful for assisting locomotion using appendages, such as human limbs, which perform a gait cycle on a solid surface. The device comprises:

(a) a lower surface, (b) a first planar spring plate positioned below the horizontally extending support and mechanically connected to the horizontally extending support, the spring plate having a proximal end, a distal end, a lateral side between the proximal end and the distal end, a medial side between the proximal end and the distal end, an upper surface, and a lower surface, the proximal end of the horizontally extending support and the proximal end of the spring plate are separated by a vertical extent; and (c) a ventral pivot positioned below the spring plate and mechanically connected to the spring plate, wherein the ventral pivot is positioned between the lateral side and the medial side of the first planar spring plate distally of a point on the first planar spring plate which receives a ground reaction force during a first portion of the gait cycle.

The present device also preferably further includes a dorsal pivot positioned between and mechanically connected both to the horizontally extending support and to the spring pivot, the dorsal pivot is positioned proximally of the ventral pivot. The dorsal pivot and ventral pivot can comprise an outer surface having a cross-sectional shape which can be, for example, elliptical, hemispherical, tubular, square, or contoured, and can also be hollow. One or more toe pivots can also be attached to the lower surface of the first planar spring plate at a point located distally of the ventral pivot.

The horizontally extending support can be made from a material selected from the group consisting of carbon fiber, metal, ethylene vinyl acetate, nylon, polyethylene, polypropylene, polyurethane, carbon fiber, or fiberglass. The horizontally extending support can also form a cradle configured to receive a human foot, and the distal end of the cradle preferably extends to a point above the first planar spring plate which is proximal to a point on the first planar spring plate which receives a ground reaction force during a second portion of the gait cycle, preferably adjacent to a point below the ball of a subject's foot.

The first planar spring plate is made from a material selected from the group consisting of carbon fiber, polycarbonate plastic, and steel, preferably carbon fiber including KEVLAR fiber and/or fiberglass. It can also be made from a plurality of materials, where each of the plurality of materials has a different property selected from the group consisting of spring coefficient, modulus of elasticity and tensile strength. The distal end of the first planar spring plate can also comprise a downwardly extending convex form, the convex form is preferably hemispherical.

In additional embodiments, the present device can be attached to a vertically extending support having a proximal end and a distal end, the distal end being mechanically connected to the upper surface of the horizontally extending support. By attaching a handle to the proximal end of the vertically extending support, a crutch can be formed. By attaching a brace to the proximal end of the vertically extending support, an AFO can be formed. A prosthesis can further be formed by connecting a receptacle for an amputated limb to the distal end of the vertically extending support. The distal end of the vertically extending support can also be mechanically connected to a mechanical device such as a robot or bionic mechanism.

FIGURES

Figure 2A:
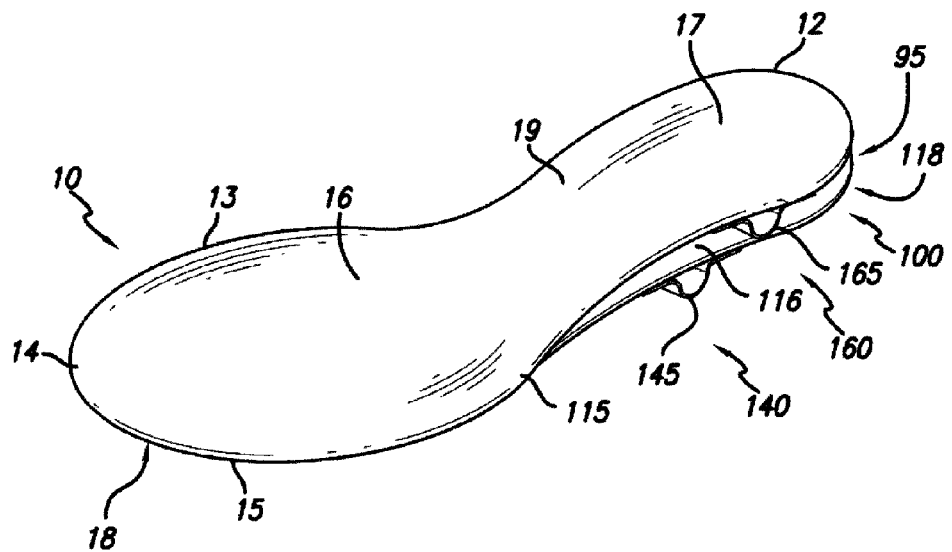

FIG. 2A a front perspective view of a further embodiment of the present spring orthotic device.

Figure 2B:
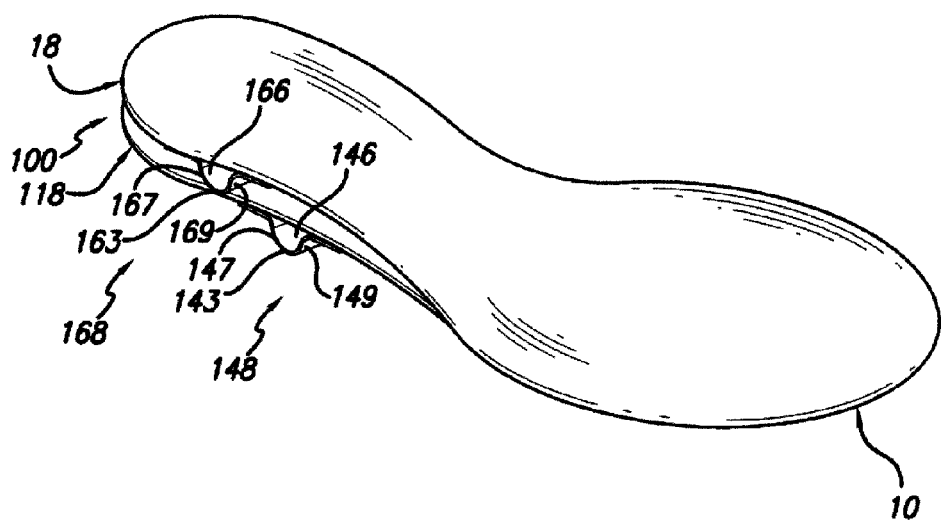

FIG. 2B is a rear perspective view of the spring orthotic of FIG. 2.

Figure 3A:
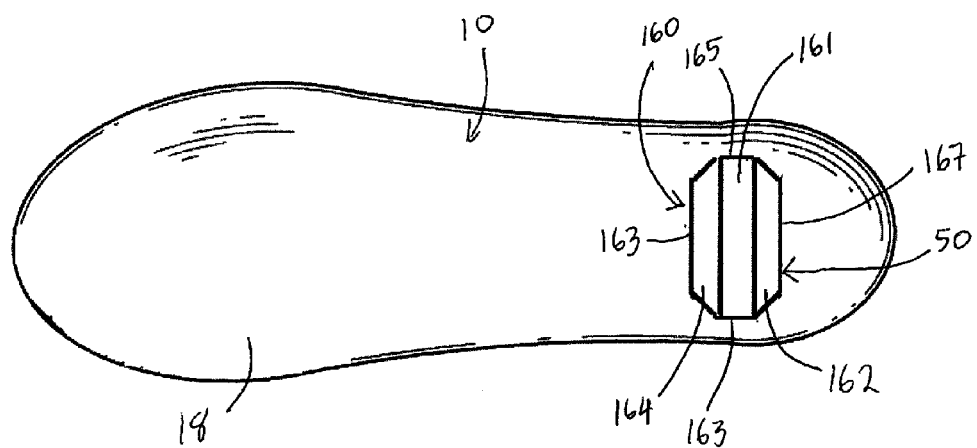

FIG. 3A is a top plan view of the underside of a cradle in one embodiment of the present spring orthotic device.

Figure 3B:
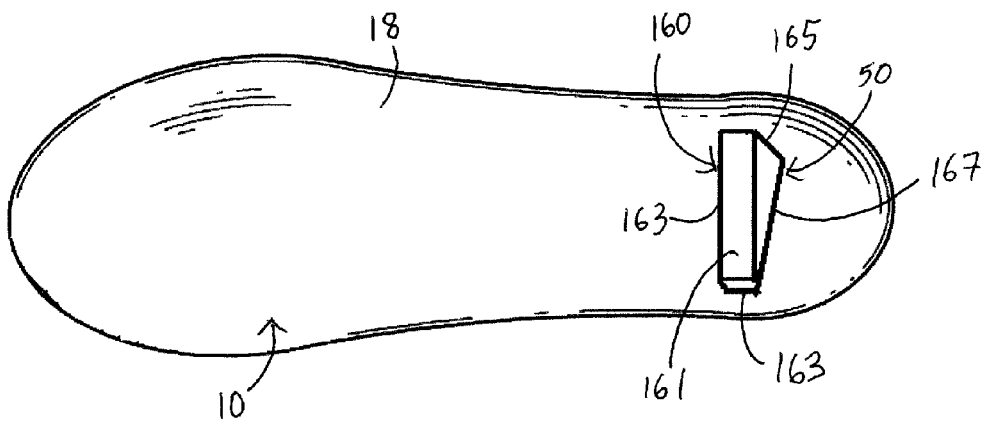

FIG. 3B is a top plan view of the underside of a cradle in an alternative embodiment of the present spring orthotic device.

Figure 3C:
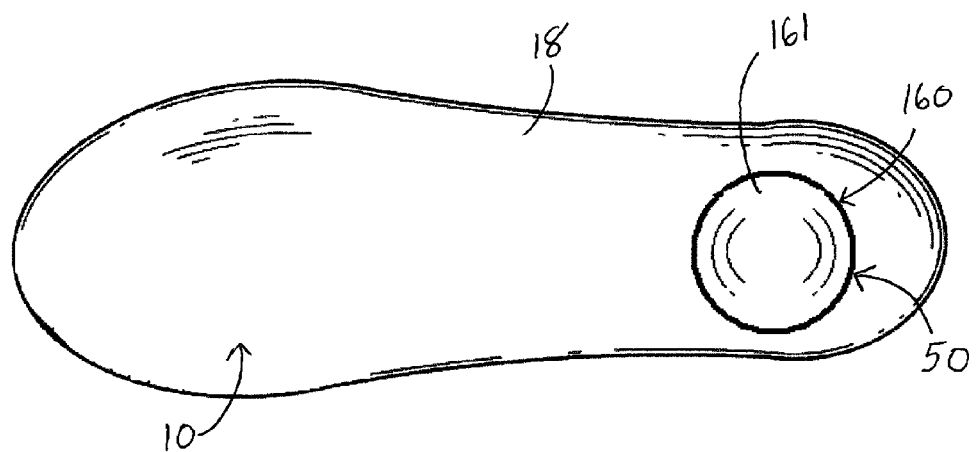

FIG. 3C is a top plan view of the underside of a cradle in another alternative embodiment of the present spring orthotic device.

Figure 4A:
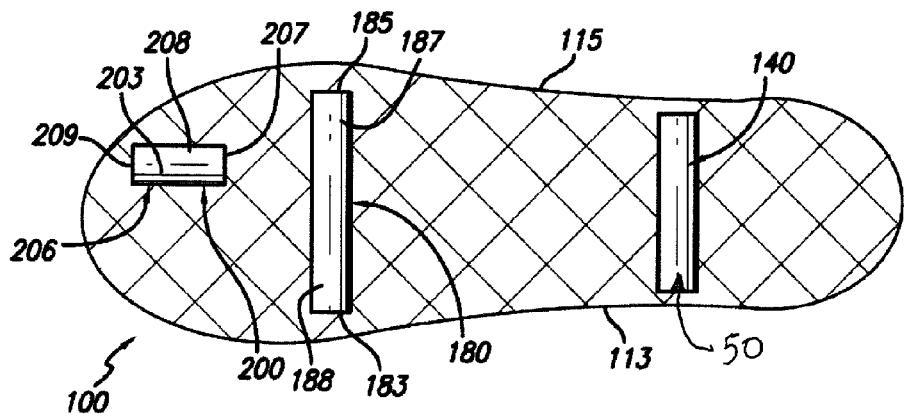

FIG. 4A is top plan view of the underside of a spring plate in one embodiment of the present spring orthotic device.

Figure 4B:
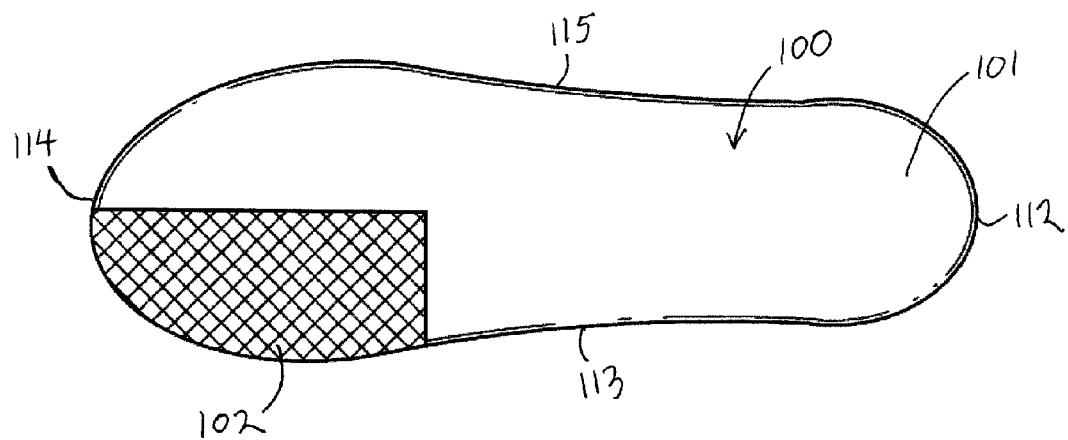

FIG. 4B is a top plan view of an embodiment of a spring plate.

Figure 4C:
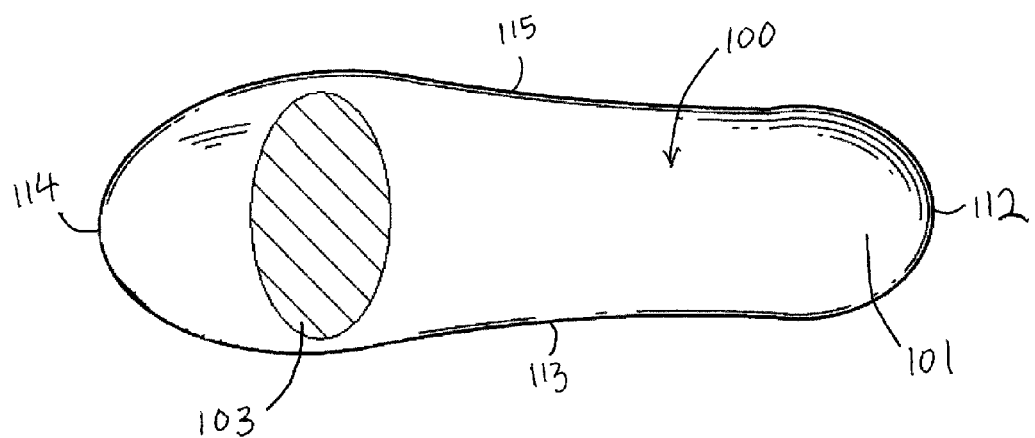

FIG. 4C is a top plan view of another embodiment of a spring plate.

Figure 4D:
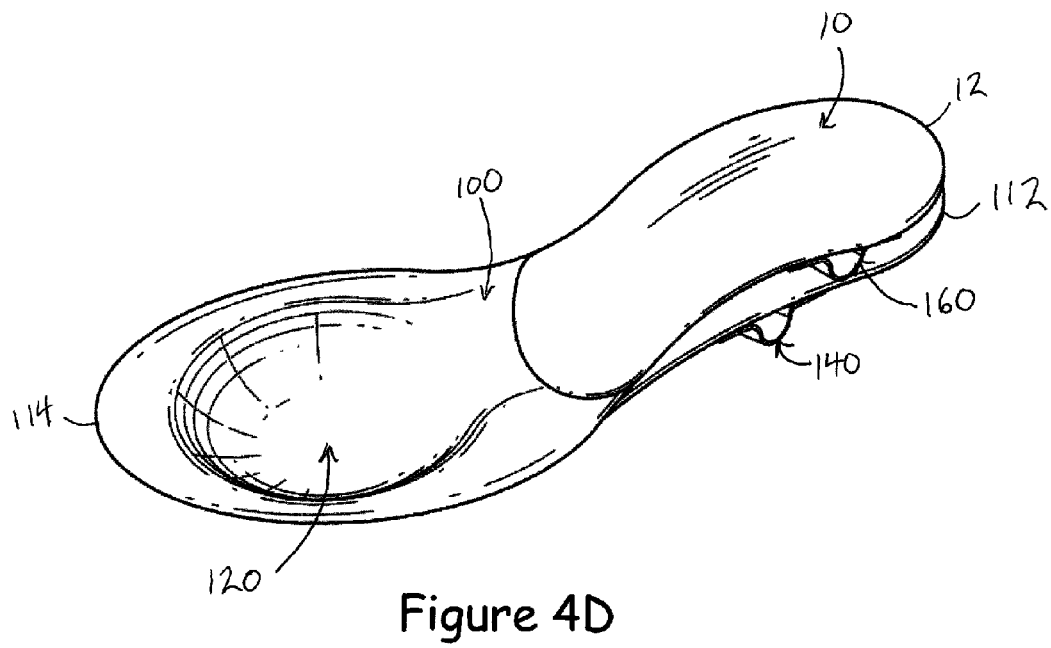

FIG. 4D is a perspective view of an embodiment of the present spring orthotic device having a shear-reducing configuration.

Figure 4E:
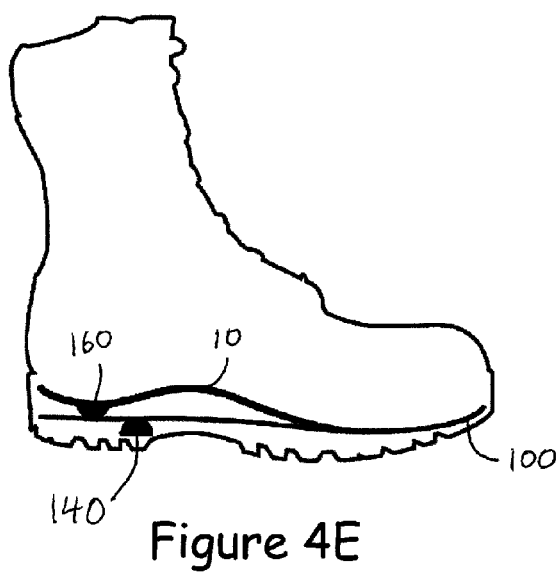

FIG. 4E is a side cutaway view of an embodiment of the present spring orthotic device in a boot.

Figure 4F:
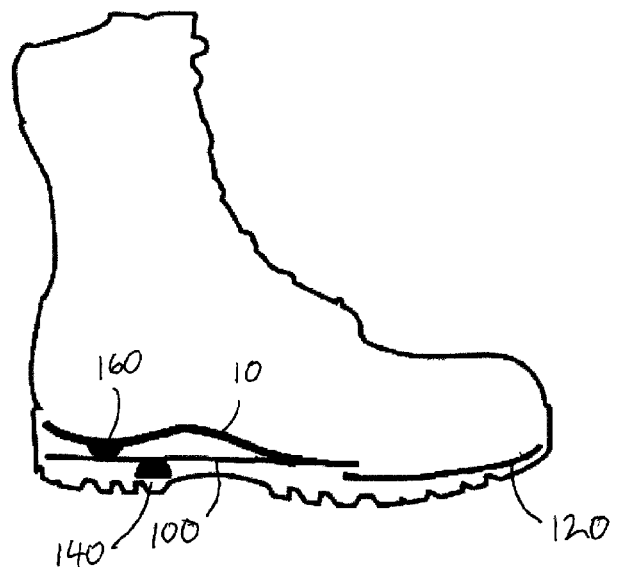

FIG. 4F is a side cutaway view of another embodiment of the present spring orthotic device comprising a forefoot spring in a boot.

Figure 4G:
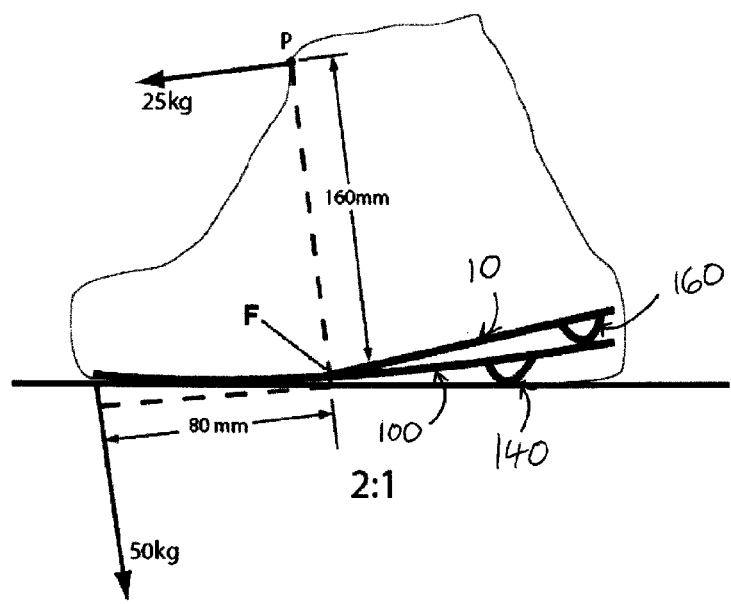

FIG. 4G illustrates the mechanical advantage provided by use of the present spring orthotic device with footwear.

Figure 5A:
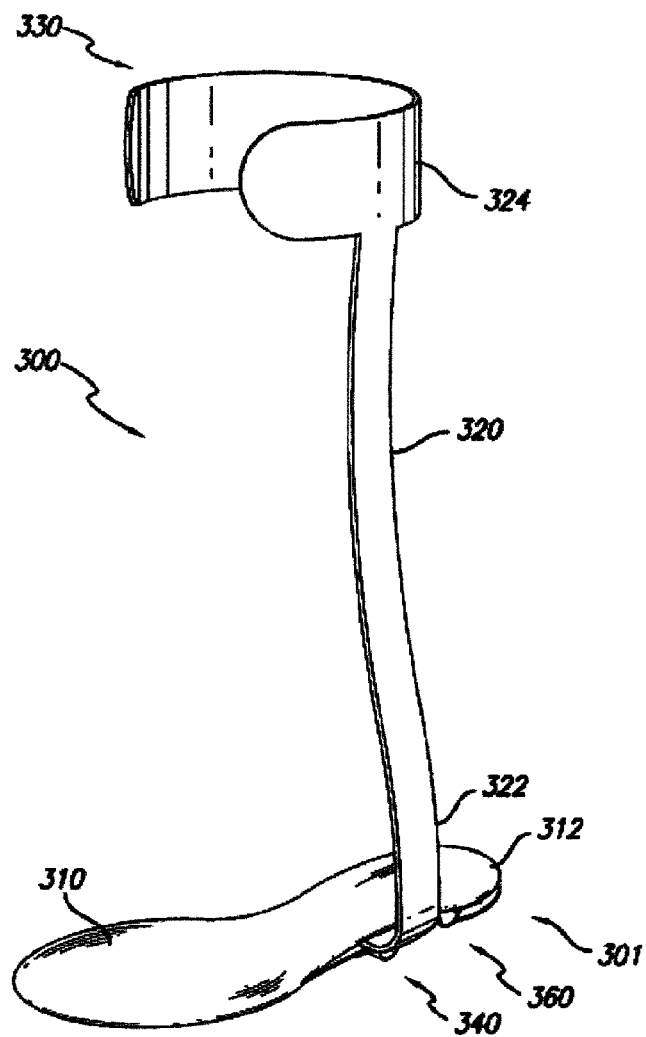

FIG. 5A is a perspective view of an ankle foot orthosis incorporating the present spring orthotic device.

Figure 5B:
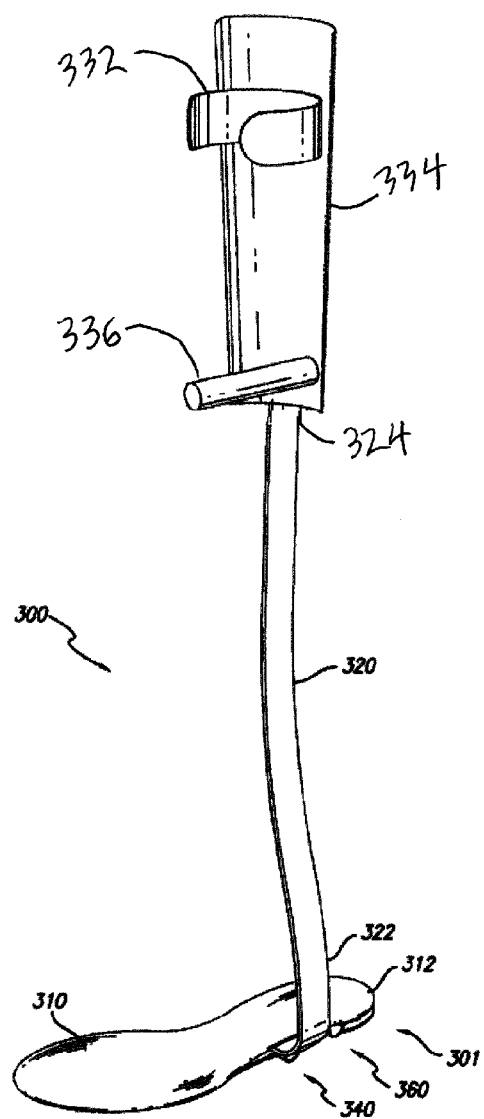

FIG. 5B a perspective view of an alternative ankle foot orthosis incorporating the present spring orthotic device.

Figure 6A:
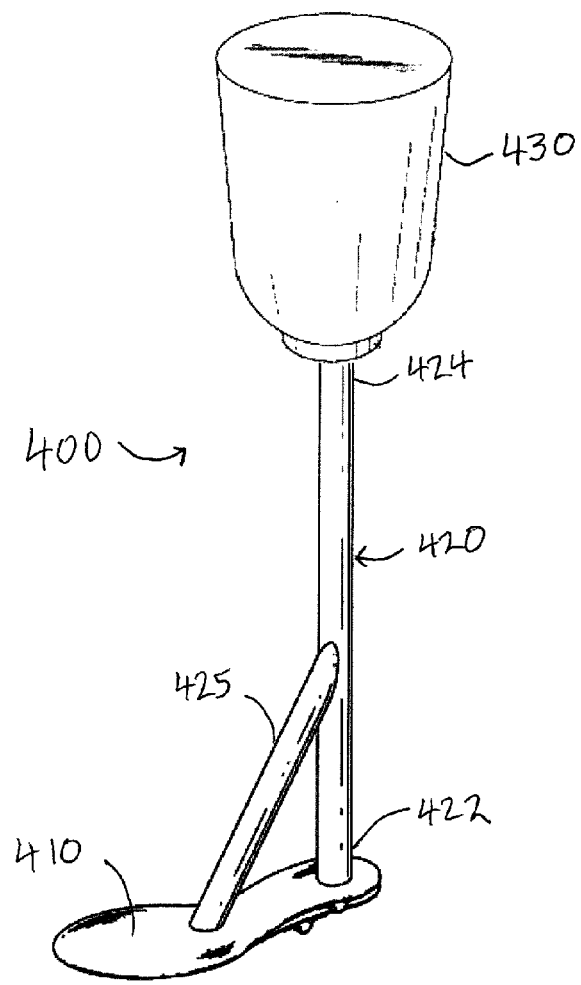

FIG. 6A is a perspective view of a prosthetic embodying the present spring orthotic.

Figure 6B:
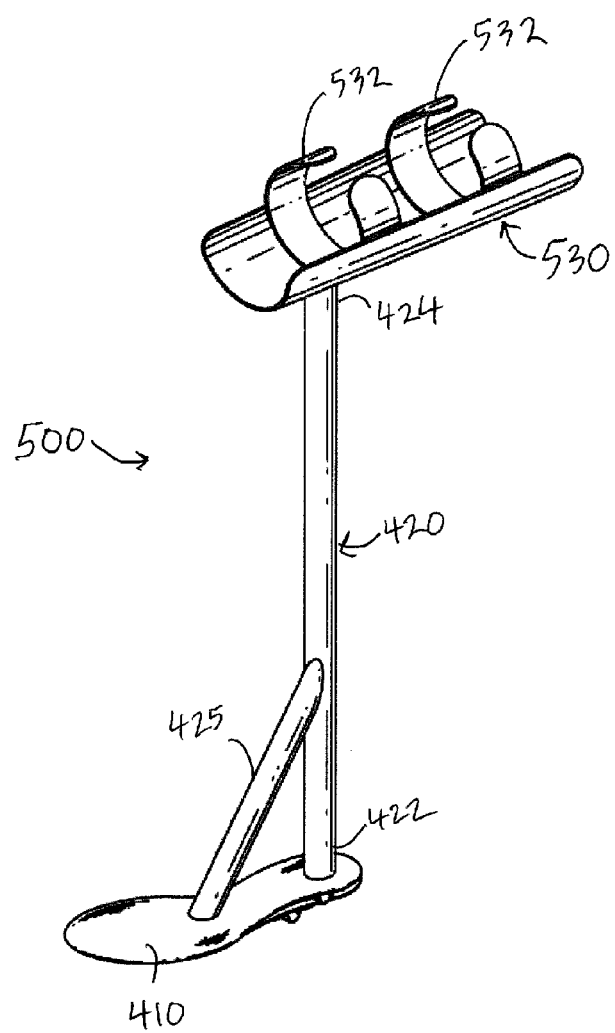

FIG. 6B is a perspective view of a knee-walker embodying the present spring orthotic.

Figure 7A:
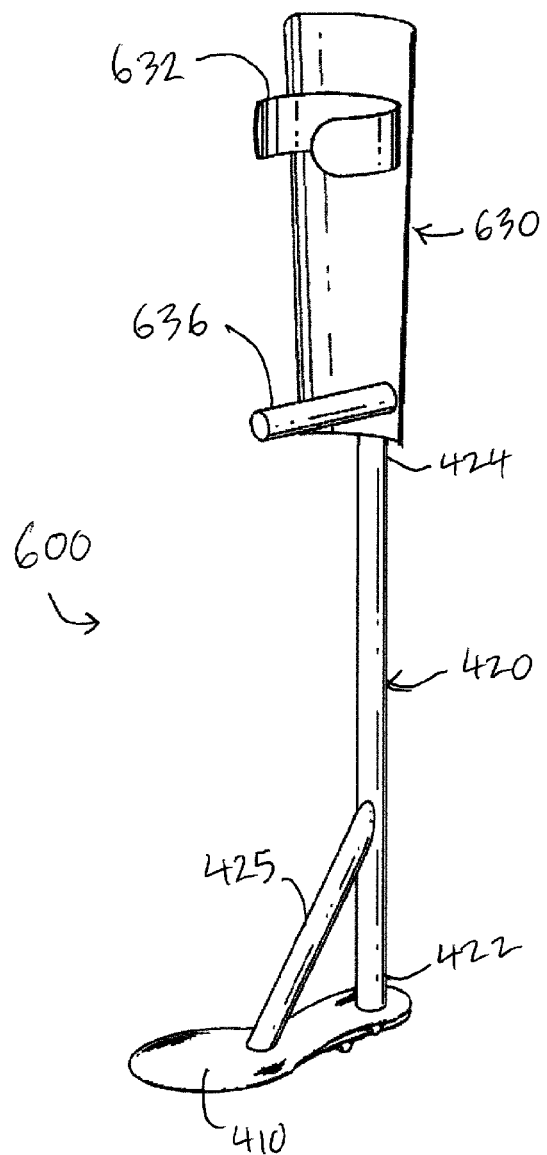

FIG. 7A is a perspective view of a crutch embodying the present spring orthotic device.

Figure 7B:
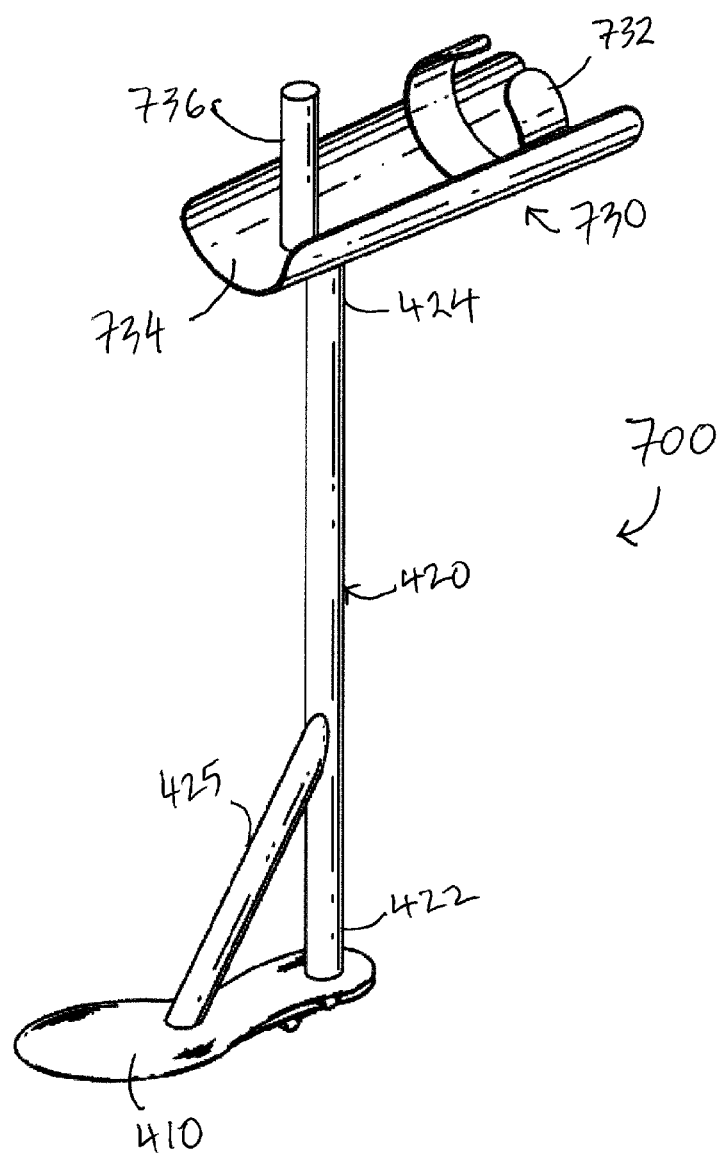

FIG. 7B a perspective view of an alternative crutch embodying the present spring orthotic device.

Figure 7C:
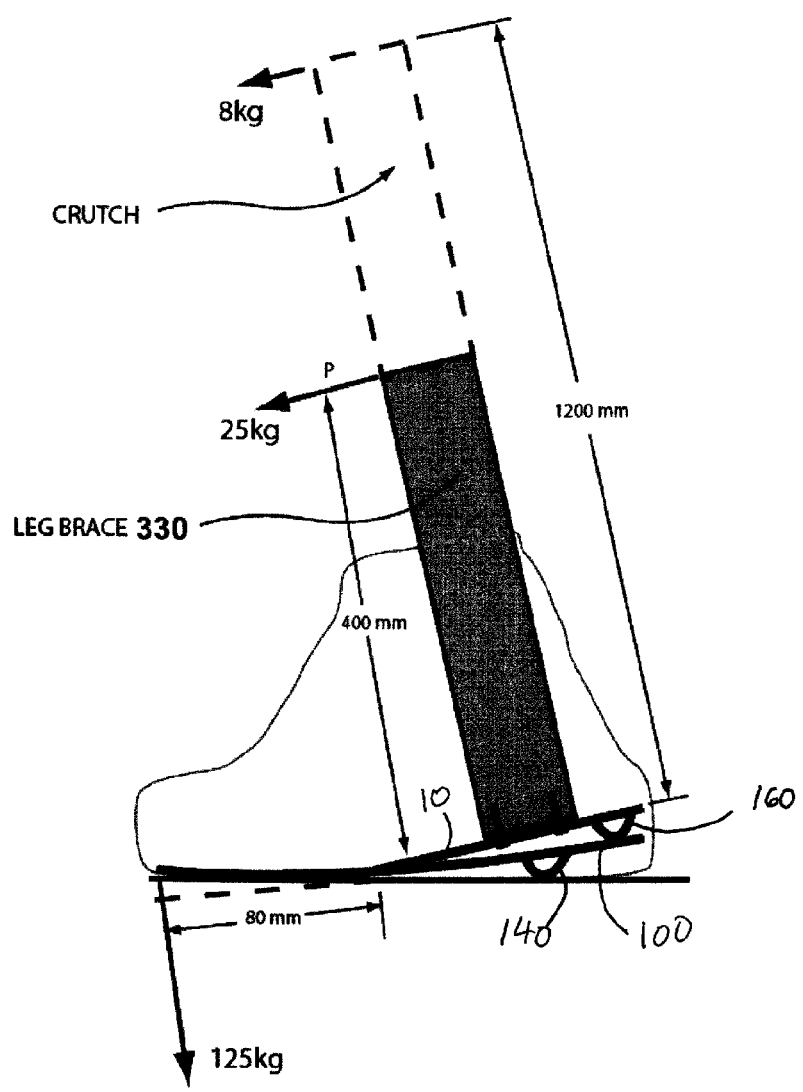

FIG. 7C illustrates the mechanical advantage provided by use of the present spring orthotic device with ankle foot orthoses and crutches.

Figure 8:
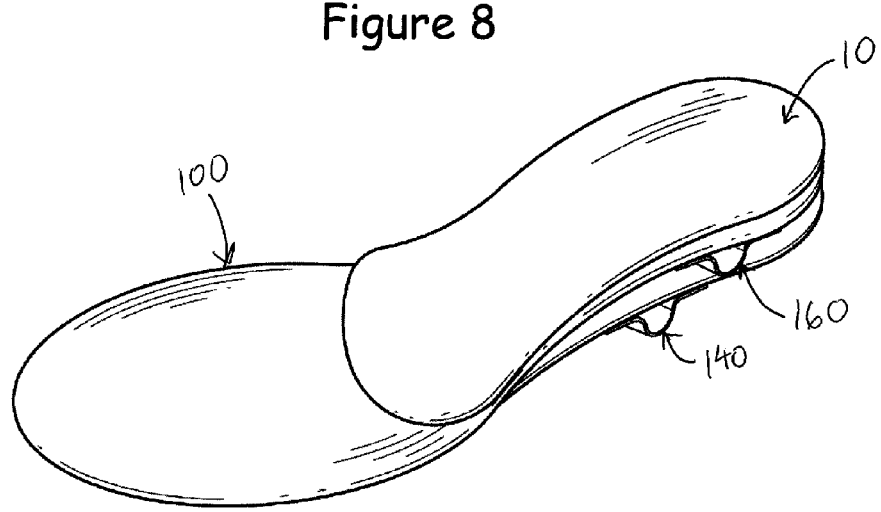

FIG. 8 is a top perspective view of an embodiment of the present spring orthotic device having enhanced puncture resistance.

Figure 9:
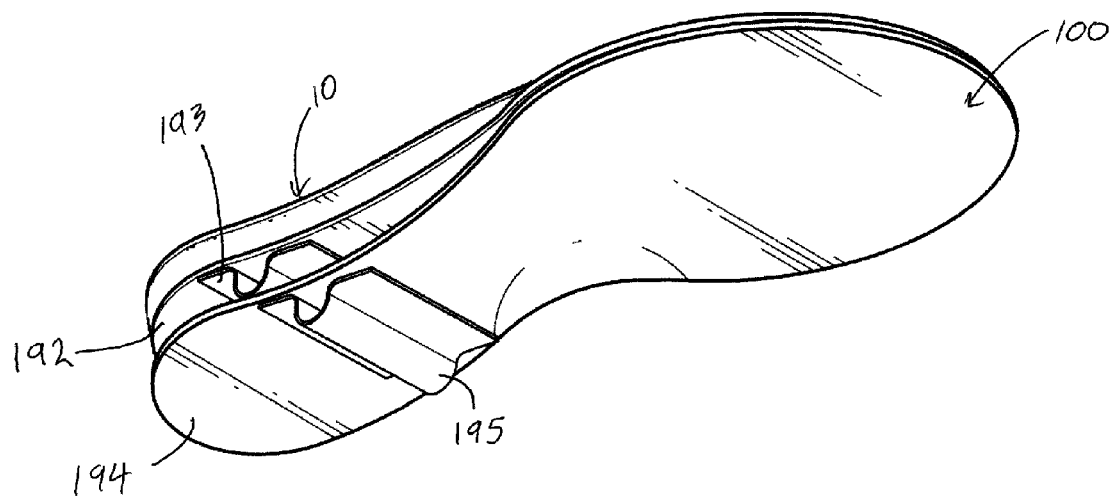

FIG. 9 is a bottom perspective view of an embodiment of the present spring orthotic device which makes use of two spring plates.

Figure 10:
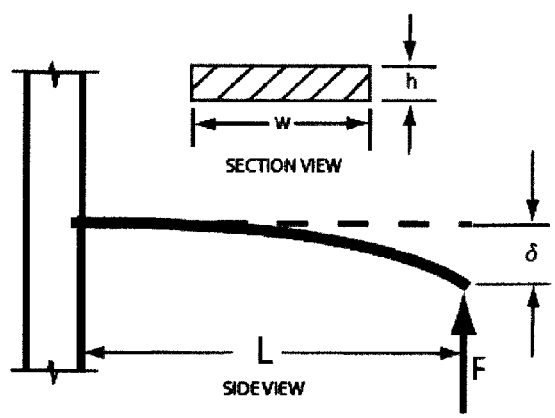

FIG. 10 is a diagram illustrating the force exerted on the heel of a preloaded spring plate in the present spring orthotic device.

FIGS. 11-15 illustrate the operation of the present spring orthotic device.

Figure 16:
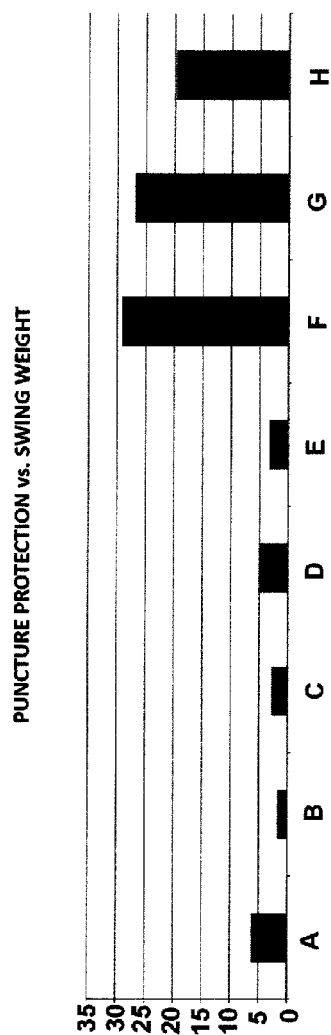

FIG. 16 is a chart showing the results of vertical jump tests including footwear incorporating the present spring orthotic device.

Figure 17:
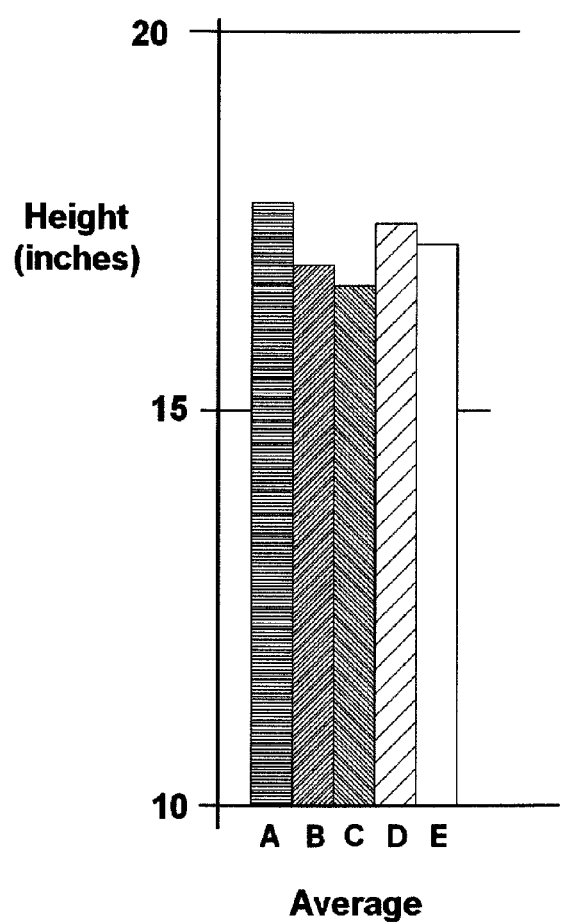

FIG. 17 is a chart showing the results of standing broad jump tests including footwear incorporating the present spring orthotic device.

Figure 18:
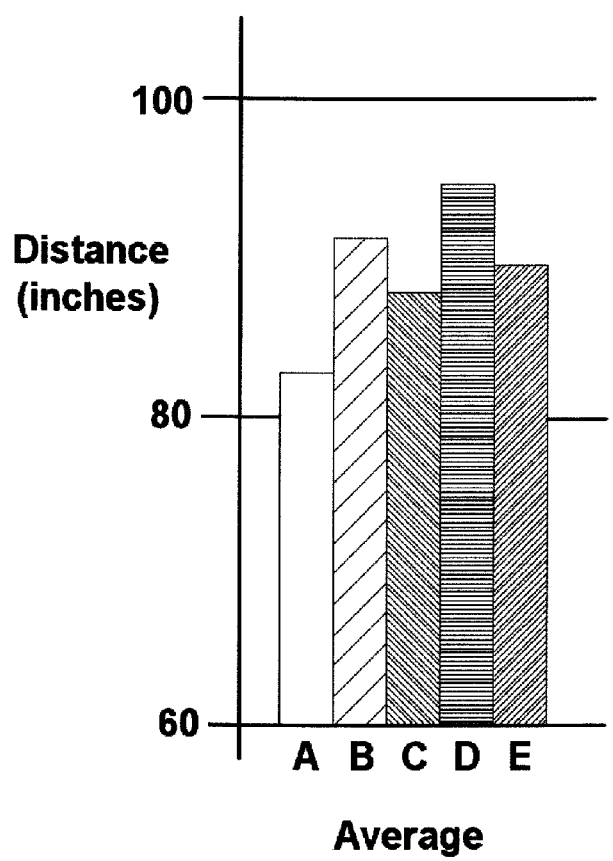

FIG. 18 is a chart showing the results of a standing board jump test conducted with an embodiment of the present invention.

DESCRIPTION

Definitions

As used herein, the following terms and variations thereof have the meanings given below, unless a different meaning is clearly intended by the context in which such term is used.

"Above" and "below," with respect to components of one of the present devices, describe the positioning of these components when the device is placed for use on the ground or other surface on which the present device is intended to be used. For example, a spring plate as described herein is below a cradle to which it is connected when the underside of the spring plate faces the ground and/or a shoe in which the device is placed.

"Ankle-foot orthoses" (AFOs) are orthoses or braces encompassing the ankle joint and all or part of the foot.

"Appendage" refers to a projection attached or otherwise connected to an individual's body or to a mechanism or other structure. The appendages referred to herein are appendages used for locomotion, such as limbs (e.g., legs or arms supported by crutches) or supports for a locomoting mechanism. Such appendages are generally hingedly connected to the body or the mechanism.

The "arch" or "arches" of the foot refer to the arches formed by the tarsal and metatarsal bones and by associated ligaments and tendons which enable the support of weight by a foot.

"Axis" refers to a point or line around which something bends or rotates, in particular around which a portion of a spring plate bends in the present devices.

"Ball" of the foot refers to the padded portion of the sole of the human foot between the toes and the arch, on which the weight of the body rests when the heel is raised.

"Calcaneal tuberosity" is the inferior and posterior extremity of the calcaneus, or os calcis, forming the projection of the heel.

"Carbon fiber" refers to a material consisting of extremely thin fibers about 0.005-0.010 mm in diameter and composed mostly of carbon atoms. The carbon atoms are bonded together in microscopic crystals that are aligned in a generally parallel manner with respect to the long axis of the fiber. The crystal alignment makes the fiber strong for its size. Several thousand carbon fibers can be twisted together to form a yarn, which can be used by itself or woven into a fabric. Carbon fiber has many different weave patterns and can be combined with a plastic resin and wound or molded to form composite materials such as carbon fiber reinforced plastic (also referred to as carbon fiber) to provide a high strength-to-weight ratio material.

"Composite material" is a material made from two or more constituent materials with significantly different physical or chemical properties which remain separate and distinct on a macroscopic level within a finished structure.

"Cradle" as used herein means a horizontally extending rigid or semi-rigid structure which provides support to one or more pivots located below the cradle. When used in foot orthotic embodiments of the present invention, the cradle can have an upper surface that conforms to at least a portion of the underside of a human foot, in the manner of the upper surface of an orthotic device inserted into a shoe to help stabilize the foot and ankle. In some embodiments, the upper surface of the cradle is formed to match the shape and curvature of a particular user's foot, as described below, while in other embodiments the upper surface of the orthotic can comprise a shape which generally matches the shape of the underside of the foot of at least a subset of users. The cradles used in the present devices are rigid.

"Crutch" is a rigid support for supporting a human subject during locomotion using a limb or body part other than the legs or feet.

"Dorsal" means away from the ground when the ventral surface of the cradle and spring plate of the present spring orthotic device faces toward the ground.

"Foot" is the lower extremity of a leg or other support used by a subject for locomotion.

"Foot orthotic" refers to an orthotic which assists a lower extremity (foot, ankle, knee or leg) in locomotion.

"Footwear" refers to shoes, boots, and other coverings worn on the feet for protection against the environment and/or for adornment.

"Gait" refers to the physical actions taken by a subject in the process of walking, running, or other forms of locomotion achieved using appendages such as human limbs.

A "gait cycle" is a series of actions performed repetitively to accomplish locomotion using appendages. A gait cycle is measured from one event (e.g., heel strike, when the use of feet is involved) to the next occurrence of the same event with the same appendage.

"Ground reaction force" means a force exerted by the ground on a body in contact with it.

"Ground" as used herein can refer to any solid surface on which the present device and/or footwear comprising the present device comes into contact with, including floors, sidewalks, dirt, rocks, and other surfaces on which a user of the present devices ambulates.

"Handle" refers to a projection or other appendage of an object that is designed to be held in order to use or move the object.

The "heel" of a foot refers to the rearward (opposite the direction of normal movement) end of a foot, which in the human foot is the padded portion of the sole behind the arch.

"Heel strike" refers to the moment of the gait cycle when the heel of a subject (or of a shoe covering the subject's foot) first contacts the ground during forward locomotion.

"Horizontal" means in a direction roughly parallel or within 30°, more preferably within 15°, of the ground.

"Impact disease" refers to one or more medical conditions of a subject that result from the force of impact of a subject's feet on the ground during locomotion, or for which such force is a contributing factor. Such diseases include plantar fasciitis, achilles tendonitis, patellar tendonitis, tibialis posterior, tendonitis, compensated pes planus, osteoarthritis, tenosynivitis, hip and sacral iliac dysfunction, spondylolisthesis, and lower back pathology.

"Insole" refers to the part of a piece of footwear on which a user's foot rests.

"Lateral" means toward the outside of a foot, i.e. toward the side on which the smallest ("pinky") toe is normally located.

"Locomotion" refers to movement by an individual subject.

"Mechanically connected" means physically connected, either through a connection based on direct physical contact or via another mechanical structure. The dorsal heel pivot described below, for example, provides a mechanical connection between the cradle and the spring plate of the present device, in some embodiments. A mechanical connection can include the use of adhesives or other means of securing structures that are mechanically connected.

"Medial" means toward the inside of a foot, i.e. toward the side on which the big toe is normally located.

"Midsole" refers to a portion of a piece of footwear located between an insole and an outsole of the piece of footwear.

"Orthotic" means a device that is applied externally to a part of the body to support a part of the body, correct a deformity, relieve pain, and/or improve the function of a part of the body.

"Outsole" refers to the outer sole of a shoe or boot that includes the bottom of the shoe and makes contact with the ground.

"Pivot" refers to a rigid member or structure, such as a shaft, beam or protuberance, which supports another structure that bends or turns around an axis defined by the length of the pivot, and which is subject to bending stresses, generally from a direction perpendicular to its length.

"Planar" refers to a structure which extends primarily in two dimensions, i.e. in which the length and width of the structure are each greater than the thickness, preferably at least 5 times greater, more preferably at least 10 time greater, and even more preferably at least 20 times greater.

"Prosthetic" refers to a mechanical device that replaces a missing body part.

"Shoe," as used herein, refers to a foot covering which provides support or protection for a foot, including therapeutic foot coverings such as foot braces, as well as conventional shoes such as boots, dress shoes, and athletic shoes. Shoes can also cover prosthetic feet.

"Spring plate" refers to a planar device comprising one or more materials that can be elastically deformed to store mechanical energy.

"Subject" refers to a user of a spring orthotic device as described herein. Subjects normally are human, though uses of the present system by an animal or a mechanical device are also possible.

"Toe-off" refers to the moment of the gait cycle when the last contact occurs between a subject's foot (or a shoe or device below the subject's foot) and the ground during forward locomotion.

"Ventral" means toward the ground when the ventral surface of the cradle and spring plate of the present spring orthotic device faces toward the ground.

"Vertical" refers to a direction toward or away from the ground, and not horizontal.

As used herein, the term "comprise" and variations of the term, such as "comprising" and "comprises," are not intended to exclude other additives, components, integers or steps. The terms "a," "an," and the and similar referents used herein are to be construed to cover both the singular and the plural unless their usage in context indicates otherwise.

Foot Orthotic Device

Figure 1A:
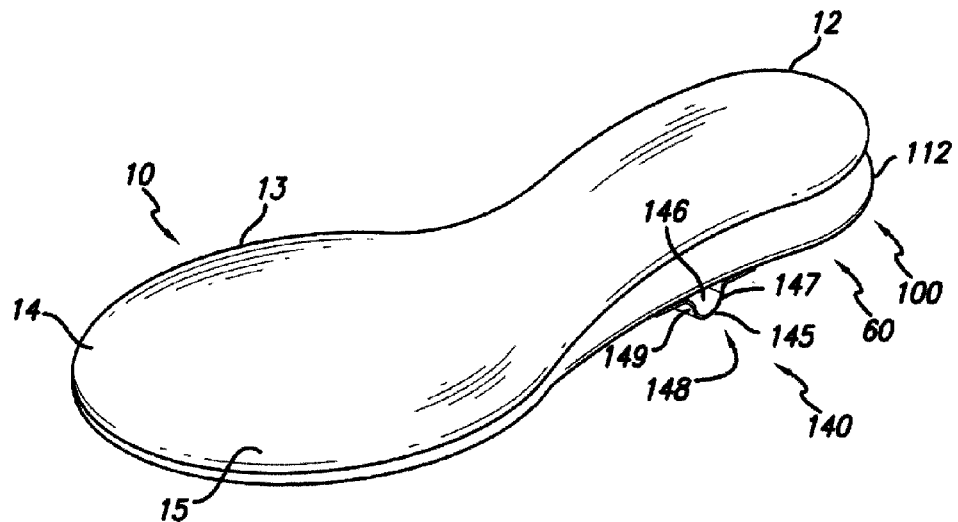
FIG. 1A is a perspective view of an embodiment of the present spring orthotic device.

FIG. 1A illustrates one embodiment of the present spring orthotic device. In this embodiment, the present spring orthotic comprises a cradle 10, at least one pivot 50, and a spring plate 100. The cradle 10 is formed from a rigid or semi-rigid material and includes a proximal end 12, a distal end 14, a medial end 13, a lateral end 15, and a generally planar dorsal surface 16. The dorsal surface 16 has a width between its medial end 13 and lateral end 16, and a length between the proximal end 12 and distal end 14, which is sufficient to contact and provide support for the lower or ventral surface of the heel of a user's foot.

Preferably, the dorsal surface 16 of the cradle 10 is shaped to match the contour of at least the heel portion of a user's foot, and in an embodiment in which the cradle 10 extends distally to contact the toes of a user's foot, such as the embodiment of FIG. 1A, the cradle 10 is preferably also shaped to match the contour of the remainder of the underside of a user's foot. That is, the dorsal surface 16 of the cradle 10 comprises a shape which is the inverse of the shape or contour of the underside of a user's foot, as shown in FIG. 1A. In other embodiments, such as that of FIG. 1B, the cradle 10 extends only from a heel portion at a proximal end 12 to point proximal of the toes (when the cradle is worn by a user), and preferably adjacent to or proximal of the ball of a user's foot, although preferably the cradle 10 extends sufficiently distally so as to support the arches of a user's foot. A cradle which extends to a point proximally of the metatarsal heads of a user's foot lowers pressure under the metatarsal heads and can reduce stress fractures.

In such embodiments, the dorsal surface 16 of the cradle 10 is preferably formed to match the underside of a specific user's foot. In this case, the cradle 10 can be formed from a polymer material such as ethylene vinyl acetate and shaped in the same manner as polymer orthotics are currently shaped to match the contour of a user's foot. In other embodiments, the dorsal surface of the cradle can alternatively comprise a shape which is the inverse of the shape of an average user's foot, i.e., which can include a concave heel depression 17 and a raised arch portion 19, the arch 19 being located distally of the heel depression 17 and including a surface which is higher than the lowest point of the heel depression 17, as measured when the present spring orthotic is placed on the ground or in a shoe with the ventral surface 18 of the cradle facing towards the ground.

In a further alternative, the dorsal surface 16 of the cradle 10 can comprise a different shape, and in some cases, can be flat. The dorsal surface 16 can also be therapeutically contoured, biomechanically balanced or otherwise modified in order to implement a therapeutic correction. In some embodiments the dorsal surface 16 of the cradle 10 comprises a surface which matches the contour of the underside of a user's foot and to contact as much of the surface of the underside of a user's foot as possible or practical, which is advantageous because the ground reaction force exerted against the underside of a user's foot is thereby spread across as much of the surface area of the underside of the user's foot as possible, thereby lowering the amount of force exerted against any particular point on the underside of the user's foot.

In order to facilitate the spreading of ground reaction forces across the underside of the surface of a user's foot, the cradle 10 is preferably formed from a rigid or semi-rigid material, such as carbon fiber, metal, ethylene vinyl acetate, nylon, polyethylene, polypropylene, polyurethane, carbon fiber, or fiberglass. Such materials generally have a shear modulus of at least about of 0.001, more preferably of at least about 0.05, and even more preferably of at least about 0.1, though it can be higher, with greater rigidity preferred.

In a preferred embodiment, the cradle is formed from a material which resists being punctured. For example, a cradle can be formed from a plurality of layers of carbon fiber material, preferably including one or more layers that incorporate KEVLAR para-aramid synthetic fiber. Preferably, such a cradle includes 2 or more layers of carbon fiber material that comprises KEVLAR fiber, more preferably 4 or more layers, and even more preferably 8 or more layers. In view of the stiffness of carbon fiber, when carbon fiber or other relatively rigid materials are used in this embodiment, the cradle preferably extends distally no further than a point adjacent the ball of a user's foot, in order to allow a user to walk normally. Such cradles can be several millimeters thick in order to provide protection to the proximal portion of a user's foot, such as between 2 and 8 mm thick, more preferably between 4 and 7 mm thick. Such a cradle is illustrated in FIG. 8. The present spring orthotic device and/or footwear which incorporates the present spring orthotic device in this embodiment also preferably meets the puncture resistance standards of ASTM designation F 2412-05 (Standard Test Methods for Foot Protection, as approved Mar. 1, 2005, published March 2005).

Located below the ventral surface 18 of the cradle 10 is a spring plate 100. The spring plate 100 comprises a proximal end 112, a distal end 114, a medial side 113, a lateral side 115, a dorsal surface 116 and a ventral surface 118. The spring plate 100 is generally planar in configuration, and is formed from a material which is preferably less rigid than the cradle 10 and has a higher modulus of elasticity. Although all of the spring plates 100 described herein comprise a single sheet of generally planar material, it will be understood that a plurality of pieces of material which are mechanically connected to each other or to another structure so as to be deformable around an axis or axes defined by pivots 50 and which are oriented in a generally planar configuration can also be used as a spring plate in connection with the present spring orthotic device.

The spring plate 100 is mechanically connected to the cradle 10 at a point which distal of the proximal end 112 of the spring plate 100, and also preferably at least at another point at or proximal of the distal end 114 of the spring plate 100. In the embodiment shown in FIGS. 1A and 1B, the ventral surface 18 of the cradle 10 is in direct contact with the dorsal surface 116 of the spring plate 100. However, in other embodiments, such as that of FIGS. 2A and 2B, the cradle 10 and spring plate 100 can be connected adjacent the proximal ends 12 and 112 via another mechanical structure, such as the dorsal heel pivot 160 shown in FIGS. 2A and 2B.

An important feature of the present spring orthotic is that a vertical distance must be maintained between the proximal end 112 of the cradle 10 and the proximal end 112 of the spring plate 100 in the absence of a load placed on the cradle. This allows the proximal end 112 of the spring plate 100 to be biased upwardly, i.e., towards the ventral surface 18 of the proximal end 12 of the cradle 10 during the heel strike portion of a user's gait. When the spring plate 100 is biased in this fashion, it absorbs some of the ground reaction force during heel strike. Moreover, the energy absorbed by the spring plate 100 is then released as a user's weight shifts from the heel to the toe portion of the user's foot during the gait cycle, thus facilitating ambulation.

Figure 1B:
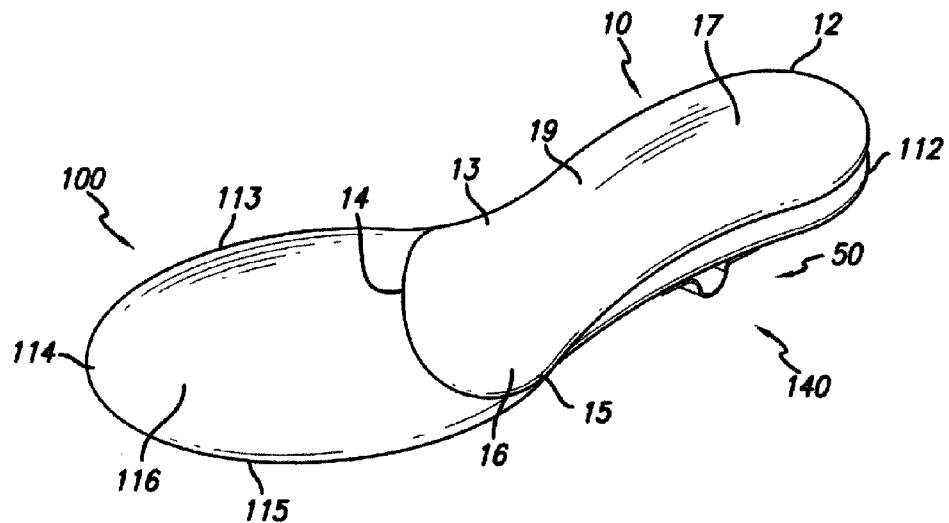
FIG. 1B is a perspective view of another embodiment of the present spring orthotic device.

In view of the need to maintain a distance between the proximal end 12 of the cradle 10 and the proximal end 112 of the spring plate 100, in the embodiment of FIGS. 1A and 1B the ventral surface 18 of the cradle 10 extends upwardly from the dorsal surface 116 of the spring plate 100 from the point at which it contacts the spring plate 100, and the cradle 10 should be formed from a material which is sufficiently rigid to maintain a distance when a user's heel exerts downward force against the cradle 10 during at least a portion of the gait cycle. In the embodiment of FIGS. 2A and 2B, the distance between the proximal end 12 of the cradle 10 and the proximal end 112 of the spring plate 100 is maintained, at least in part, by the dorsal heel pivot 160 which is adjacent to the proximal ends of the cradle 10 and spring plate 100 and which is positioned in between them.

The contact point between the ventral surface 18 of the cradle 10 and the dorsal surface 116 of the spring plate 100 in the embodiments of FIGS. 1A and 1B serves as an axis about which the spring plate 100 can bend when upward ground reaction forces are exerted against the proximal end 112 of the spring plate 100. The amount of deformation experienced by the proximal end 112 of a spring plate 100 over the distance that the proximal end 112 travels before contacting the underside of the cradle 10 should be within the elastic limit of the spring plate 100.

Positioned below the spring plate 100 is a ventral heel pivot 140 having a medial end 143, a lateral end 145, a dorsal surface 146, a ventral surface 148, a proximal end 147, and a distal end 149. The ventral heel pivot 140 provides a second axis about which bending of the spring plate 100 occurs. When a downward force is exerted by the heel of a user on the cradle 10, a portion of that force is exerted proximally of the ventral heel pivot 140 and causes the spring plate 100 to bend downwardly, i.e., such that the ventral surface 118 at the proximal end 112 of the spring plate 100 becomes closer to the ground.

The ventral heel pivot 140 and other pivots 50 are preferably longitudinal, preferably extending across at least 70% of the width of the spring plate 100, and more preferably extending across at least 90% or across all of the width of the spring plate 100, although in some embodiments a plurality of pivots 50 can be used to form an axis around which the spring plate 100 can bend. The pivots 50 illustrated in FIGS. 2A and 2B have an elliptical or hemispherical cross-section, but differently shaped pivots can also be used, for example tubular pivots, bars having a square cross section, contoured pivots, or pivots of other shapes. One of skill in the art can determine an appropriate shape and material for the pivots 50, depending on the properties of the spring plate 100 and on the placement of the pivots within the present spring orthotic.

The pivots 50 can be hollow, as illustrated in FIGS. 2A and 2B, if they are formed from a sufficiently rigid material (in order to reduce the weight of the present spring orthotic), but they can also be formed of a solid piece of material. In one embodiment, the dorsal heel pivot 160 can be integrally molded with the cradle 10. One advantage in using hollow pivots, in particular convex hollow pivots, is that they can provide additional impact protection to a user by being designed to break or deform at a pressure which is less than the pressure at which the bones in a user's foot would break, thereby protecting the user from fractures, including stress fractures in the bones of the foot.

In some embodiments, the ventral heel pivot 140 can comprise a part of a shoe, such as a part of the sole of a shoe, with which the spring plate 100 is mechanically connected. In such embodiments, the portion of the shoe below the proximal end 112 of the spring plate 100 would provide sufficient clearance, i.e. vertical space between the ventral side 118 of the spring plate 100 and the bottom of the shoe, to allow the proximal end 112 of the spring plate 100 to bend vertically downward when downward pressure is exerted on it, such as by the heel of a user during the heel strike portion of the gait cycle.

The ventral heel pivot 140 preferably extends longitudinally across at least a portion of the width of the spring plate 100, i.e., between the medial side 113 and lateral side 115 of the spring plate 100. The longitudinal extent of the ventral heel pivot 140, i.e., the distance between the medial end 143 and the lateral end 145, is preferably sufficient to allow the entire width of the spring plate 100 to bend evenly around the axis point created by the ventral heel pivot 140 when downward heel pressure is exerted by the heel of a user. This is to allow more of the spring plate to bend, thereby providing more spring force to be harnessed when downward pressure is exerted by the heel of a user on the spring plate 100. The ventral heel pivot 140 should, for this reason, also be sufficiently rigid to allow the spring plate 100 to bend around the axis point created by the ventral heel pivot 140. During the heel strike portion of the gait of a user, when downward heel pressure is applied to the proximal end 112 of the spring plate 100, the axis point created by the ventral heel pivot 140 is at or adjacent to the proximal end 147 of the ventral heel pivot 140.

In the foregoing description, it can be seen that the spring plate 100 of the present spring orthotic device undergoes a double bending during the heel strike portion of the user's gait, thus absorbing a greater amount of force than would be the case if the spring plate 100 were bent around only a single axis. The first bending, around an axis created by the ventral heel pivot 140, occurs due to the downward force exerted by the heel of a user's foot, while a second bending can occur, in the embodiment of FIGS. 1A and 1B, around the axis point created by the point in which the ventral surface 18 of the cradle 10 contacts the dorsal surface 116 of the spring plate 100. In the embodiment of FIGS. 2A and 2B, the second bending axis occurs at or adjacent the ventral surface 168 of the dorsal heel pivot 160 where the dorsal heel pivot 160 contacts the spring plate 100.

In a preferred embodiment, illustrated in FIGS. 2A and 2B, a second pivot 50, namely the dorsal heel pivot 160, is placed between the ventral surface 18 of the cradle 10 and the dorsal surface 116 of the spring plate 100. The dorsal heel pivot 160 is placed at the desired axis point which is proximal of the axis point created by the ventral heel pivot 140. The dorsal heel pivot 160 preferably has similar physical and structural characteristics as the ventral heel pivot 140, and can be made from the same or a similar material as the ventral heel pivot 140. The dorsal heel pivot 160 likewise comprises a dorsal surface 166 which is mechanically connected to the ventral surface 18 of the cradle 10 and a ventral surface 168 which is in mechanical connection with the dorsal surface 116 of the spring plate 100. The dorsal heel pivot 160 further comprises a medial side 163, a lateral side 165, a proximal end 167, and a distal end 169.

Preferably, the dorsal heel pivot 160 is located adjacent the proximal end 112 of the spring plate 100, in order to provide only a relatively short distance between the proximal end 167 of the dorsal heel pivot 160, where the bending axis occurs, and the proximal end 112 of the spring plate 100. As described above, by providing such a shorter distance, less leverage is exerted against the proximal end 112 of the spring plate 100, and the spring plate 100 is thus able to absorb a greater ground reaction force over a shorter bending moment. In a preferred embodiment, the dorsal heel pivot 160 is within about four centimeters of the proximal end 112 of the spring plate 100, and in a more preferred embodiment, the dorsal heel pivot 160 is within about one centimeter of the proximal end 112 of the spring plate 100.

The peak pressure point on a user's heel is at the point on the surface of the heel which is below the calcaneal tuberosity. Therefore, in preferred embodiments, the dorsal heel pivot 160 is placed vertically below the calcaneal tuberosity, when the user's heel is in contact with the dorsal surface 16 of the cradle 10. In embodiments in which the dorsal surface 16 of the cradle 10 includes a heel depression 17, the dorsal heel pivot 160 is thus placed below the center of the concave surface creating the heel depression 17 in order to best position the dorsal heel pivot 160.

The dorsal heel pivot 160 preferably has a length greater than its width, and the length of the dorsal heel pivot preferably extends from a point at or adjacent to the medial end 13 of the cradle 10 to a point at or adjacent to the lateral end 15 on the dorsal surface 16 of the cradle 10. The length of the dorsal heel pivot 160 is also preferably approximately perpendicular to the longitudinal axis of the cradle 10. The embodiments of FIGS. 1A-2B employ such a pivot, in which the pivot is rounded along its longitudinal axis such that spring plate 100 bends smoothly along the surface of the dorsal heel pivot 160. Rounded pivots are generally preferred in embodiments using a carbon fiber spring plate 100, as the use of sharper angles in the pivots 50 may tend to break the carbon fibers in such embodiments. In other embodiments, the length of the dorsal heel pivot 160 pivot can be angled with respect to the longitudinal extent of the cradle 10, such as at an angle of 5°, 10°, 15°, 30°, or other desired angles.

In alternative embodiments, such as that shown in FIGS. 3A-3C, the dorsal heel pivot 160 can comprise one or more flat or curved surfaces along its longitudinal extent. In the embodiment of FIG. 3A, a lower, flat surface 161 is provided which contacts and is preferably secured to the spring plate 100. A proximal flat surface 162 extends proximally from the lower surface 161 of the pivot to the ventral surface 18 of the cradle 10, while a ventral flat surface 164 extends distally from the lower surface 161 of the pivot to the ventral surface 18 of the cradle 10. Providing flat surfaces which meet at a defined angle, such as surfaces 161 and 162 in FIG. 3A, allows the spring plate 100 to bend more sharply and affects the spring characteristics of the present spring orthotic device. The angle can be 90°, or can be an acute angle as shown in FIG. 3A, such as an angle of 20°, 30°, 45°, or other desired angles. In addition, a plurality of flat surfaces joined at a defined angle can also be provided between a lower surface 161 and the ventral surface 18 of the cradle 10 in order to provide different spring characteristics.

In the embodiments of FIGS. 1A-3A, dorsal heel pivots 160 are shown in which the lower surfaces 161 of such pivots are approximately parallel to the dorsal surface 18 of the cradle 10 along their longitudinal extents. FIG. 3B shows a further alternative embodiment of a pivot, in which the pivot is elevated on one lateral side as compared with the other lateral side of the heel pivot, such that the lower surface 161 forms an oblique angle with respect to the dorsal surface 18 of the cradle 10. In the illustrated embodiment, lateral side 165 extends further from the dorsal surface 18 than medial side 163, although embodiments in which medial side 163 extends further from the dorsal surface 18 than lateral side 165 are also possible. The embodiment of FIG. 3B can assist in correcting inversion and eversion (pronation) of the foot, and can also help to stabilize the ankle and elevate a foot's arch.

In addition to dorsal heel pivots 160 with flat surfaces, such pivots can alternatively comprise alternative shapes which comprise or include contoured surfaces, as in the embodiment of FIG. 3C. In this embodiment, the dorsal heel pivot comprises a lower surface which is hemispherical in shape. Pivots 50 in this embodiment allow for ankle strengthening and flexibility of the leg and hip.

In some embodiments, it can also be advantageous to include bracing, i.e. a rigid support attached or otherwise mechanically connected to the spring orthotic device. Such bracing provides further mechanical advantage and increases the efficiency of the device, and can assist in preventing a user's heel from lifting up, i.e. losing contact with and separating from the surface of the cradle 10 of the device or from an insole above the cradle.

Sprint Plates

One of the advantages of the present spring orthotic is in reducing the peak ground reaction force exerted against the underside of a user's foot in a situation when the user has experienced an injury or other damage to the foot, in particular, damage caused by obesity, diabetes, competitive sport, and exercise. By reducing the ground reaction force exerted against the underside of such a user's foot and transmitted into a user's body, the present spring orthotic devices reduces pain and further injury or damage to the user's foot and/or other parts of the body (such as the ankle, hip, knees, and lower back). In view of the additional benefit to users who are of greater than average weight, the spring plate 100 is preferably configured to absorb greater than 2%, more preferably greater than 10%, and even more preferably greater than 50% of the ground reaction force exerted against an individual of greater than average weight (currently about 72 kilograms for a woman and 86 kilograms for a man in the U.S.). More preferably, the spring plate 100 can be configured to absorb similar ground reaction forces for individuals in the 95th percentile of the weight of individuals in the population, or between about 113 and 122 kilograms. In some instances, the spring connectors can be configured to absorb ground reaction forces of an individual of even greater weight, such as a weight of 80 kilograms.

The spring plate 100 of the present spring orthotic device is formed from a material which can be elastically deformed by the forces exerted against the device during locomotion in order to store and then release mechanical energy. A spring plate 100 can be formed from any of a number of materials that can flex in order to store and release mechanical energy, including plastics such as polycarbonate plastics and metals such as steel. However, in preferred embodiments, the spring plate 100 is formed from a composite material such as carbon fiber. For example, glass and carbon fiber composite laminates can be used to form the present spring plate 100. Materials having a large ratio of Modulus of Elasticity:density are desirable due to an increase in the stiffness of the material with a reduction in weight. Table 1 below illustrates the favorable ratio of Modulus of Elasticity:density that can be provided by carbon fiber materials:

TABLE 1

Modulus of Elasticity vs. Density

| Material | Ultimate Tensile Strength (MPa) | Density (g/cm³) | Modulus of Elasticity (GPa) | Modulus of Elasticity vs. Density Ratio |
|---|---|---|---|---|
| Natural Diamond | 1048 | 3.21 | 703 | 326 |
| Carbon Fiber Composite | 758 | 1.68 | 221 | 451 |
| Carbon Steel A-36 | 448 | 7.83 | 206 | 57 |
| Bone | 172 | 1.49 | 14 | 115 |
| Polycarbonate Plastic | 68 | 0.83 | 2.3 | 82 |
| Rubber | 7 | 1.38 | 0.03 | 5 |

In a further embodiment, illustrated in FIG. 4A, the spring plate of the present spring orthotic can comprise further pivots 50, such as a ventral ball pivot 180 and/or a toe pivot 200. The ventral ball pivot 180 includes a medial end 183, a lateral end 185, a dorsal surface 186, a ventral surface 188, a proximal end 187, and a distal end 189. The ventral ball pivot 180 is positioned in connection with the ventral surface 118 of the spring plate 100 in a like manner as the ventral heel pivot 140, but is located distally of the ventral heel pivot 140. As a user's gait transitions to the toe-off portion of the gait cycle, the ventral ball pivot 180 provides an axis at around its distal end 189 around which the spring plate 100 can bend and thereby absorb ground reaction force exerted against the distal or ball portion of a user's foot. Preferably, the ventral ball pivot 180 is positioned under the metatarsal heads of a user's foot. Additionally, a dorsal ball pivot can be provided between the spring plate 100 and the cradle 10, either proximally or distally of the ventral ball pivot 180, in order to provide the advantages of a double spring, as described above.

The toe pivot 200 illustrated in FIG. 4A differs from the foregoing pivots 50 in that its longitudinal extent is between its proximal end 207 and its distal end 209, i.e., the longer portion of the toe pivot is placed in a direction which is roughly perpendicular to that of the foregoing pivots, and roughly parallel to the forward direction in which a foot travels during the gait cycle, i.e. to the longitudinal extent of the present spring orthotic. More importantly, the longitudinal extent of the toe pivot 200 is oriented so as to provide an axis along the longitudinal extent around which bending occurs in a side to side direction, i.e., so as to absorb ground reaction forces exerted preferentially on one side of a user's foot. During the toe-off portion of the gait cycle, greater downward forces can be exerted against one side of the user's foot (either the medial or lateral side, depending on the particular subject) than against the other side. The toe pivot 200 is thus preferably located so that it provides an axis around which the medial side 113 and/or the lateral side 115 of the spring plate 100 can bend downwardly during the toe-off portion of the gait cycle. In other embodiments, the longitudinal extent of the toe pivot can be angled with respect to the longitudinal extent of the spring plate 100, such as at an angle of 5°, 10°, 15°, 30°, or other desired angles. Toe pivots 200 can assist in controlling inversion and eversion of the forefoot, i.e. supination and pronation. In other embodiments, such longitudinally extending pivots can be positioned at the proximal end of the present device, i.e. adjacent proximal end 112 of the present spring plate 100, in order to control inversion and eversion of the rear portion of a user's foot.

In embodiments of the present spring orthotic which incorporate pivots 50 having a length and width of different dimensions, such as the pivots 50 shown in FIGS. 3A, 3B, and 4A (having a length greater than their width), the pivots 50 can be mounted on the cradle 10 and/or on the spring plate 100 in a horizontally rotatable but securable fashion. In this embodiment, the pivots can be rotated about a fixed axis (either a central axis or an axis adjacent to a longitudinal end of the pivot) in order to change the spring characteristics of the present spring orthotic device. The pivots are reversibly securable, so that they can be rotated but then secured in a fixed position on the cradle 50 and/or on the spring plate 100. Alternatively or in addition, the pivot or pivots 50 can be vertically adjustable, i.e. to adjust the vertical height of a pivot. Horizontal and/or vertical adjustment of a pivot can be accomplished, for example, using a ratcheted mechanism in which the pivot comprises receptacles, teeth or other projections which engage receptacles, teeth or other projections on or attached to a cradle 10 or spring plate 100, thereby forming a toothed mechanism which rotates the pivot. In this way the pivot can be adjusted in three dimensions.

The ventral heel pivot 140 and dorsal heel pivot 160, as well as other pivots as disclosed herein, can also be of different shapes, sizes, and dimensions, in order to provide a customized device which meets the needs of a particular individual. For example, a spring orthotic having a dorsal heel pivot 160 of greater height than the ventral heel pivot 140 can provide a longer, softer contact between the spring plate 100 and the lower surface which it contacts. In another embodiment, a spring orthotic having a ventral heel pivot 140 of greater height than the dorsal heel pivot 160 can provide a bigger lever radius and allow more mechanical work to be done by the present device.

FIG. 4B illustrates an embodiment of a spring plate which allows greater downward forces to be exerted against one side of a user's foot during the toe-off portion of the gait cycle than against the other side. In this embodiment, this is accomplished by producing a spring plate which has a different spring coefficient, modulus of elasticity and/or tensile strength on one lateral side of the spring plate as compared to the other lateral side of the spring plate 100. In the embodiment of FIG. 4B, the portion of the spring plate 100 at the proximal end 112 and lateral side 115 of the spring plate 100 is composed of a first material 101 while the medial side 113 of the distal end 114 is composed of a second material 102 having a different spring coefficient, modulus of elasticity and/or tensile strength. Alternatively, the spring plate 100 can be made from a uniform material, but can be formed with a portion (e.g., area 102 in FIG. 4B) which is thicker or thinner than another portion of the spring plate 100, or to which another material has been joined.

This same concept is applied in a different manner in the embodiment of FIG. 4C, which illustrates an alternative spring plate in which an area 103 over the ball of a user's foot stores and releases less mechanical energy as compared to surrounding portions of the spring plate 100, in order to reduce the amount of force applied to high pressure areas. For example, portion 103 can be formed with a thinner or softer material as compared to the remainder of the spring plate. Alternatively, the spring plate 100 can comprise holes in areas of the spring plate in which it is desired to reduce the force exerted against a user's foot.

In some embodiments, a more rigid area of material (i.e., having greater tensile strength and/or being less flexible) can be provided beneath the portion of a user's foot between the first metatarsal phalangeal joint. This reduces hallux dorsilexion, and in individuals suffering from arthritis in this joint this can reduce pain and inflammation of this joint. A more rigid portion of the present spring plate 100 can also advantageously be provided beneath areas in which a user has experienced an amputation or other loss of a digit, for example as a result of diabetes. The greater tensile strength can compensate for the loss of the digit or digits, and reduce pressure and/or stress on the remaining digits. In order to further reduce the peak ground reaction force exerted against the ball of a foot, the distal portion of the present spring orthotic device can be provided with a forefoot spring. The forefoot spring is preferably able to absorb at least about 2% of the ground reaction force, more preferably at least about 5%-10% of the ground reaction force, and even more preferably at least 50% of the ground reaction force which is exerted against it.

In the embodiments of the present device shown in FIGS. 1-3A and 4A-4E, the spring plates 100 extend along the length of a user's foot, and include a forefoot spring plate portion 120 below the ball of the foot of a user when the user uses the present spring orthotic device. The forefoot spring plate 120 in these embodiments is generally planar in configuration, and can be formed from the same type of material as the remainder of spring plate 100, for example from a composite material like carbon fiber. In the alternative embodiment shown in FIG. 4D, the forefoot spring plate 120 includes a downwardly extending convex form, which can be in the shape of a full or partial hemisphere. When upward ground reaction force is exerted against the lower convex surface of the forefoot spring 120, the spring deflects and absorbs some of the ground reaction force, so that the central portion of the forefoot spring plate 120 is able to deflect downwardly when pressure is exerted downwardly against its dorsal surface.

Spring plates 100 are typically placed in a piece of footwear above the outsole, as shown in FIG. 4D. In FIG. 4D, the spring plate is illustrated as being a unitary construction, in which the spring plate 100 extends along the length of a shoe. FIG. 4E however shows an alternative embodiment in which the spring plate 100 extends only to the ball of the foot, at or adjacent to where the cradle meets the spring plate 100. A separate forefoot spring then extends distally from the distal end of the spring plate 100. In this way, gait assistance can still be provided to a user while reducing or avoiding breakage of the spring plate 100 at the junction of the cradle and the spring plate 100. The forefoot spring preferably overlaps with the spring plate 100, i.e. the proximal end of the forefoot spring extends proximally beyond the distal end of the spring plate 100.

The spring plate 100 is also preferably freely retained within a piece of footwear comprising this embodiment of the present shoe orthotic, i.e. the spring plate 100 is not bonded or otherwise physically joined to the forefoot spring portion 120, although connectors linking the two structures can also be provided in ways known to the art if desired. The forefoot spring 120 can be made from the same type of material as the spring plate 100, with similar properties, or alternatively can be formed from a material having different properties than the spring plate 100. For example, the forefoot spring 120 can comprise a combination of materials as illustrated in the embodiments of FIGS. 4B and 4C, or can comprise a single material having different properties than the spring plate 100.

In a further embodiment of the present spring orthotic device, the device can comprise a plurality of spring plates 100 stacked in a vertical manner. The embodiment illustrated in FIG. 9 includes two spring plates, an upper spring plate 192 and a lower spring plate 194, although additional spring plates can be used. The first ventral heel pivot 193 of the upper spring plate 192 is positioned with respect to a dorsal heel pivot (if used) as in other embodiments of the present spring orthotic, but the lower surface of the first ventral heel pivot 193 in this embodiment is placed in contact with or otherwise mechanically connected to the upper surface of the lower spring plate 194. A second ventral heel pivot 195 in contact with or otherwise mechanically connected to the lower surface of the lower spring plate 194 is positioned proximally of the first ventral heel pivot 193, i.e. the axis around which the lower spring plate 192 bends with respect to the first ventral heel pivot 193 is located distally of the axis around which the lower spring plate 192 bends with respect to second ventral heel pivot 195. The use of additional spring plates 100 can allow larger loads to be born by the present spring orthotic device.

Operation of the Spring Orthotic

The bending moment (torque) of the proximal end 112 of the spring plate 100, i.e. the rotational force bending the spring plate 100 about an axis, is determined both by the material properties of the spring plate 100 and by the distance between the axis point 60 and the proximal end 112 of the spring plate 100 where the spring plate 100 contacts the surface on which it is placed (either the ground or a shoe, in most cases). The amount of distance between the axis 60 and the proximal end 112 determines the amount of leverage exerted on the spring plate 100, with shorter distances providing less leverage, which thereby allows the spring plate 100 to absorb a greater ground reaction force with a smaller amount of deflection (bending). The spring plate 100 should bend around axis point 60 at deflection angles of between 1° and 90°, preferably at deflection angles of between 15° and 60°.

FIG. 10 illustrates the force exerted on or by a cantilever beam, which stores potential energy when deflected by a force. The force (F) exerted on or by the proximal end 112 of a spring plate 100 can similarly be expressed as follows (Formula I):

$$F = \frac{\delta(E \times w \times h^3)}{4 \times L^3}$$

where:
L is the length of the spring plate 100 from the dorsal heel pivot 160 to the proximal end 112;
δ is the deflection;
E is the Tensile Modulus (Modulus of Elasticity);
w is the width of the spring plate 100; and
h is the height of the spring plate 100.

Figure 11:
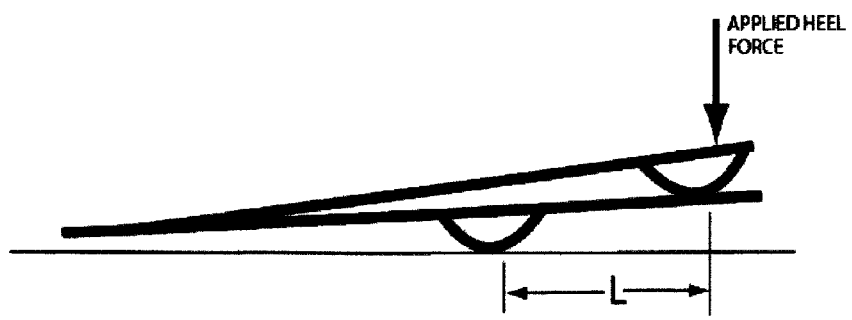
Figure 12:
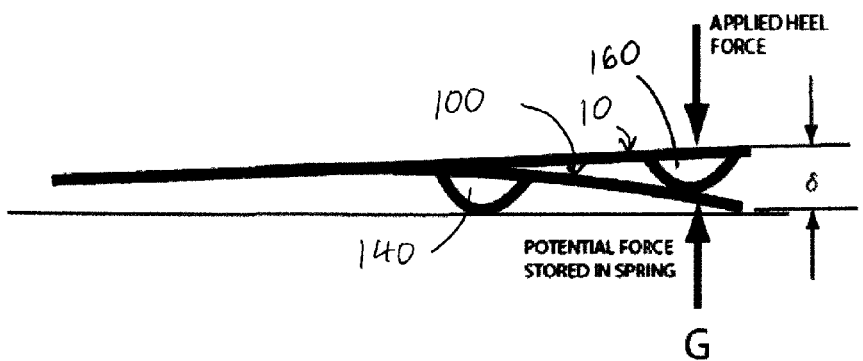
Figure 13:
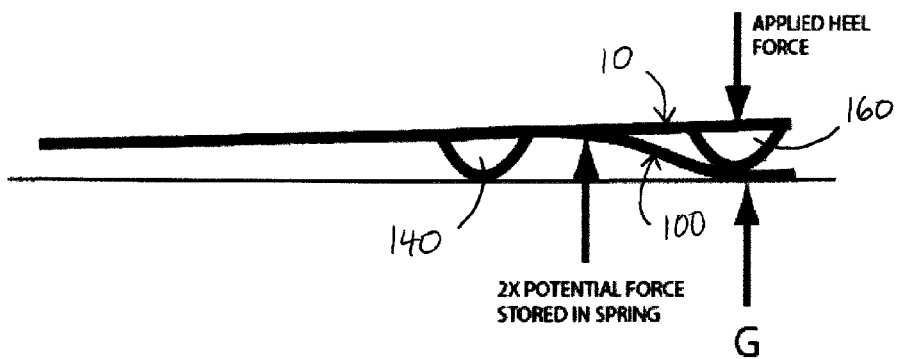

As further illustrated in FIGS. 11 and 12, when a downward stepping force is applied by the heel of a user against the cradle 10 of the present device (FIG. 10), the spring plate 100 is bent downward around ventral heel pivot 140 (FIG. 12), storing the stepping force as potential energy as tension in the material of the spring plate 100. The force of the user's heel then continues to bend the spring plate 100 downward, and when the proximal end 112 of the spring plate 100 contacts the surface directly beneath it (generally an outsole), the spring plate 100 is bent upward around the dorsal heel pivot 160 (FIG. 13) by ground reactive forces (G). This double bending of the spring plate 100 essentially doubles the potential force (lifting power) of the spring plate 100 (as calculated in Formula I above), while effectively minimizing stress on the material of the spring plate 100.

Figure 14:
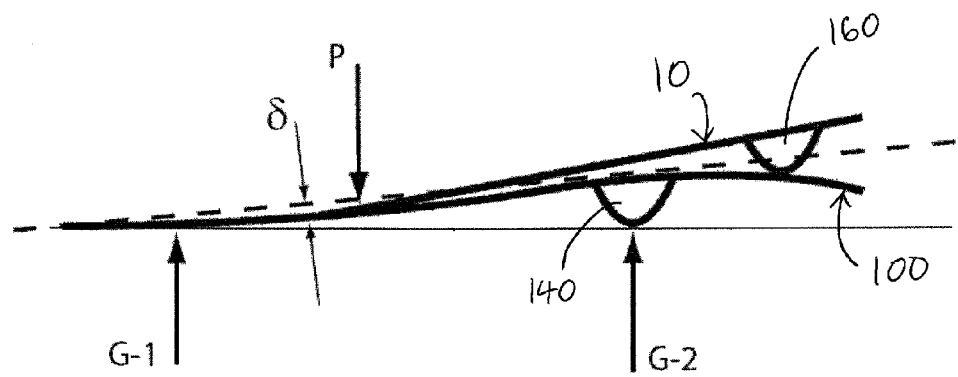
Figure 15:
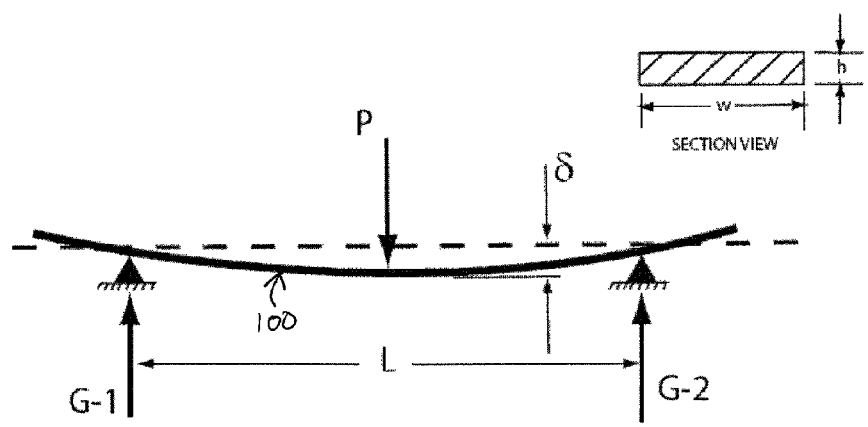

During the latter portion of a gait cycle, as the heel of a user is raised, the potential energy stored in the spring plate 100 by the application of a downward stepping force is released as the spring plate 100 returns to its pre-bending shape, helping a user of the present device to bring the foot back to a horizontal position. As shown in FIG. 14, in embodiments of the present device which incorporate a forefoot spring, the bending of the spring plate 100 around the ball of the foot (at point P in FIG. 14) due to the ground reactive forces G-1 and G-2 results in additional potential energy being stored in the spring plate 100. The potential force (P) stored in the spring plate 100 during this phase of the gait cycle can be expressed as follows (Formula II):

$$P = \frac{\delta(4 \times E \times w \times h^3)}{L^3}$$

where:
L is the length of the portion of the spring plate 100 between the points where ground reactive forces G-1 and G-2 are applied;
δ is the deflection;
E is the Tensile Modulus (Modulus of Elasticity);
w is the width of the spring plate 100; and
h is the height of the spring plate 100.

By manipulation of the dimensions of the spring plate 100, the relationship of the pivots, or the materials utilized, different "spring factors" can be achieved. For example, the formula above can be seen to be very sensitive to the distance between pivots (L). If the distance of the pivots is reduced by only 10%, the normal force exerted on the heel is increased by over 40%. The normal force exerted on the heel can also be manipulated by changing the cross-sectional shape of the spring plate, which increases the spring plates resistance to bending (moment of inertia). Increasing the thickness of the spring plate by 10% will increase the normal force nearly 35%, and doubling the thickness will increase the force by 800%.

The efficiency and energy conservation which can be achieved by the present spring orthotic device is enhanced by the leverage provided by footwear and other supports mechanically connected to the present device. As shown in FIG. 4G, when 25 kilograms of force is exerted at a point (P, at the front of the housing of a boot that includes the present device in FIG. 4G) which is 160 millimeters from a fulcrum (F) on the spring plate 100, and when the distance from the fulcrum (F) to the distal end 114 of the spring plate 100 is 80 millimeters, 50 kilograms of force is exerted at the distal end 114 of the spring plate 100. This is expressed by the following formula (Formula III):

$$F_1 \times D_1 = F_2 \times D_2$$

where:
F=the force applied; and
D=the perpendicular distance to the fulcrum.

Ankle-Foot Orthoses

The present spring orthotic device can also be incorporated into an ankle-foot orthosis in order to assist individuals having foot or leg injuries which require the need for a leg brace.

An orthosis can also be used by individuals without such injuries, as the securing of the brace portion of the orthosis above the ankle of a user can assist in harnessing more torque from the distal portion of the spring plate 100. In one embodiment, illustrated in FIG. 5A, an ankle-foot orthosis 300 comprising the spring system of the previously described spring orthotics includes a vertical support 320, a cradle 310 and a brace or fastener 330 for attaching the ankle-foot orthosis 300 to the leg of a subject. In this embodiment, the proximal end 312 of the cradle 310 is attached to (or integrally formed with) the lower end 322 of the vertical support 320. The vertical support 320, as shown in FIG. 5A, extends vertically upward from the proximal end 312 of the cradle 310, and is designed to be placed adjacent to the rearward side of a subject's leg when the ankle-foot orthosis is worn. The vertical support 320 can be made from rigid materials known to those skilled in the art, such as a carbon fiber composite or plastic, and can be made from the same material as the cradle 310 or from a different material.

The fastener 330 shown in FIG. 5A is attached to the upper end 324 of the vertical support 320. Additional fasteners 330 can also be placed along the longitudinal extent of the brace 330 in order to better secure the ankle-foot orthosis 300 to a subject's leg. The fastener 330 shown in FIG. 5A comprises a strap for placement around the leg of a subject, but can alternatively comprise other configurations or mechanisms, as known to those skilled in the art. Likewise, the vertical support 320 can be configured differently, depending on the need of the subject. In some embodiments, a second vertical support extending upward from a user's knee can be joined at a lower end by a hinged connection to the vertical support 320.

The ankle-foot orthosis 300 further includes a spring plate 301 below the cradle 310, a dorsal heel pivot 360 and a ventral heel pivot 340. The foregoing components of the ankle-foot orthosis 300 are the same as has been described previously for the spring orthotic device, and therefore are not further described in detail here. Additional pivots and the alternative configurations described previously for the present spring device can also be used with the ankle-foot orthosis 300, and therefore are also not described here.

FIG. 5B illustrates another embodiment of an ankle-foot orthosis. The lower portion of the AFO of FIG. 5B can be identical to that of FIG. 5A. In the embodiment of FIG. 5B, however, the upper portion 334 of the vertical support 320 is provided with a handle 336 and preferably also with a fastener 332. In this embodiment, a subject can partially support his or her weight by gripping the handle 336 in the manner of a crutch, in order to relieve pressure on the user's foot.

Prosthetic Devices

FIG. 6A illustrates a prosthetic device 400 which makes use of the spring system of the present spring orthotic devices. Such a leg prosthetic comprises a vertical support 420, one or more fasteners 430 at the upper end 424 of the support 420, and a horizontal support 410 at the lower end 422 of the support 420. The fastener in this case is designed to receive an amputated limb. In FIG. 6A, the fastener is a receptacle 430.

The prosthetic device 400 differs from the ankle-foot orthosis of FIG. 5A in that the fastener 430 is configured both to attach the prosthetic device 400 to the limb of subject (in this case an amputated limb), but is also designed to support an amputated limb above the ground. The vertical support 420 likewise differs from the vertical support 320 in that it must be sufficiently strong to bear at least some of the weight of an individual wearing the prosthetic device 400 above the surface of the ground.

The horizontally extending support 410 differs from the cradle 310 of the ankle-foot orthosis of FIG. 5A in that it is unnecessary for the dorsal surface 416 of the horizontal support 410 to be shaped to receive the underside of a foot. As shown in FIG. 6A, the prosthetic device 400 further comprises a spring plate 401, a dorsal heel pivot 460 and a ventral heel pivot 440 below the horizontal support 410. Although not illustrated in FIG. 6A, at least the spring plate 401, the dorsal heel pivot 460 and the ventral heel pivot 440 would typically be located within a housing, which in some embodiments can approximate the form of a human foot. Additional pivots used with the present spring orthotic and other features described above can also be used in a spring prosthetic according to the present invention.

In order to facilitate a normal gait for the user of the prosthetic device 400, the ventral heel pivot 440 and the dorsal heel pivot 460 are positioned at a proximal end of the horizontal support 410, in a manner similar to the positioning of these components in the spring orthotic described above. In the embodiment illustrated in FIG. 6A, the vertical support 420 is attached to (or integrally formed with) the horizontal support 410 at a first point which is distal to the positioning of the ventral heel pivot 440 and the dorsal heel pivot 460. However, in an alternative embodiment, the vertical support 420 can be attached to the horizontal support 410 at a position which is closer to or at the proximal end of the horizontal support 410, in a similar manner to the way that the vertical support 320 of the ankle-foot orthosis 300 connects with the cradle 310. As shown in FIG. 6A, the vertical support 420 is also connected to the horizontal support 410 at a second point distal of the first point by a cross support 425, which attaches at a proximal end to a point on the vertical support 420 which is vertically above the lower end 422, and attaches at a distal end to a point on the horizontal support 410 which is distal of the point at which the lower end 422 of the vertical support 420 attaches to the horizontal support 410. Cross support 425 can in an alternative embodiment be integrally formed with the vertical support 422 and/or with the horizontal support 410, and no space between the cross support 425 and vertical support 422 is required.

FIG. 6B illustrates another embodiment of a prosthetic device, in this case a "knee-walker" 500 or temporary replacement for a limb injured below the knee. In this embodiment, in place of a receptacle for an amputated limb, a brace 530 is attached to the upper end 424 of the vertically extending support, and one or more fasteners 532 are provided for securing a shin portion of a subject's leg to the brace 530. The brace 530 in this embodiment extends generally horizontally with respect to the vertical support 420.

Crutches and Additional Uses

FIGS. 7A and 7B illustrate crutches which make use of a vertical support 420 and other components below the vertical support 420 in the ankle-foot orthoses and prosthetic described above. These components can be used to form a crutch 600 by attaching a handle 636 at or adjacent the upper end 424 of the vertical support 420. Optionally, a fastener 432 for an arm of a subject can be provided. In the embodiment of FIG. 7A, the handle is attached to the crutch 600 approximately horizontally. In the embodiment of FIG. 7B, the handle 736 in the upper portion 734 of the crutch 700 is positioned approximately vertically, and a horizontal brace 734 for supporting an arm of a subject is provided, together with an optional fastener 732.

As illustrated in FIG. 7C, the use of the present spring orthotic device in conjunction with a crutch, ankle foot orthosis, or other mechanical arrangement that involves bracing of the device to a user's leg greatly increases the efficiency of the device and provides greater leverage. For example, when 25 kilograms of force is exerted on the illustrated brace 330, 125 kilograms of force is exerted at the distal end 114 of the spring plate 100 (a 5:1 mechanical advantage).

A longer support, such as a crutch, provides additional mechanical advantage. In the embodiment illustrated in FIG. 7C, a 15:1 mechanical advantage can be obtained with a 1200 millimeter support. In this embodiment, 8 kilograms of force exerted at the top of the crutch will result in 125 kilograms of force at the distal end 114 of the spring plate 100, i.e. a longer lever will achieve a greater mechanical advantage.

The spring system described above can, alternatively, also be used in a locomotion system for a robot or other machine or mechanical device, in particular locomotion systems which make use of supports or other appendages that are raised above the ground and then returned to the ground at a different point in a gait cycle in order to move a mechanical device. The present device can be used to reduce the impact forces experienced by such a mechanical device. This embodiment can be similar to the prosthetic device 400 illustrated in FIG. 6A, except that the vertical support 420 is attached at an upper end 424 to a part of a robotic or other mechanical system, in particular to a hinged joint of such a device. In a further alternative, the upper end 424 of the vertical support 420 can be attached to a bionic system, i.e. to mechanical or electromechanical components that augment or replace physiological functions.

Footwear

The present spring orthotic device is typically worn inside of a shoe or other piece of footwear, and can be designed to be removed from the shoe and incorporated into a different shoe. In such embodiments, the ventral side of the spring orthotic faces and/or is in contact with the dorsal side of an insole of a piece of footwear. When the present device also comprises an ankle-foot orthosis, prosthetic, or other device that supports a limb of a subject, such a device can likewise be designed to be used with a standard shoe, as in the embodiments illustrated in FIGS. 5 and 6.

In some embodiments, the present spring orthotic devices can be incorporated into shoes in an irreversible fashion, such that the shoe would have to be damaged in order to remove the device, such as by severing an adhesive or sewn connection. In such embodiments the present spring orthotic can take the place of a midsole in the shoe, as illustrated in FIG. 4C, which shows the placement of the present orthotic above the outsole of a boot.

Methods of Use

The foregoing spring orthotic devices facilitate the gait of a user by absorbing ground reaction forces, by spreading peak ground reaction forces, and by exerting force upward upon the release of energy absorbed by the spring plates of the device, thereby lessening the amount of energy needed by a user to walk. In the case of individuals who are overweight or who have experienced injuries to their lower extremities, the foregoing are important advantages.

When a spring orthotic is present in a shoe or prosthetic of a subject, the benefits of using such an orthotic begin at heel strike, when upward ground reaction force is exerted at the proximal end of a shoe in which the present device is positioned. The proximal end 112 of the spring plate 100 is biased (bent) upward around an axis at the proximal end 167 of the dorsal heel pivot 160 (or around an axis 60, in the embodiment of FIGS. 1A and 1B) by such ground reaction force at heel strike. At the same time or shortly thereafter, downward force exerted by the heel of a user on the cradle 10 biases a more distal portion of the spring plate 100 downwardly around an axis at the proximal end 147 of the ventral heel pivot 140. The bending of the spring plate 100 around the dorsal heel pivot 160 and the ventral heel pivot 140 absorbs energy, which is released later in the gait cycle.

As the gait cycle continues and the weight of the user shifts forwardly, i.e. in the direction of ambulation, ground reaction force at the proximal end of the spring orthotic lessens. When the amount of force exerted by the spring plate 100 due to the bending of the spring plate 100 around the dorsal heel pivot 160 and the ventral heel pivot 140 exceeds the ground reaction force exerted against the proximal portion of the spring plate 100, the spring plate 100 begins to bend in the opposite direction, i.e. the proximal end 112 of the spring plate 100 bends downward around the axis at the proximal end 167 of the dorsal heel pivot 160 and the more distal portion of the spring plate 100 bends upwardly around the axis at the proximal end 147 of the ventral heel pivot 140, thereby releasing its stored energy. The spring plate 100 at this point exerts an upward spring force, thereby reducing the amount of effort required by a user of the spring orthotic to complete this portion of the gait cycle.

As the weight of the user continues to shift forwardly during the gait cycle, downward force is exerted at a more distal portion of the spring plate 100. The spring plate 100 then bends downwardly around an axis at the proximal end 187 of the ventral ball pivot 180. Later in the gait cycle, as the user's weight continues to shift forward, the energy absorbed by the bending of the spring plate 100 around the ventral ball pivot 180 is exerted upwardly, further reducing the amount of effort required by a user of the spring orthotic to complete this portion of the gait cycle.

EXAMPLES

Example 1

A spring plate for use in the present spring orthotic was produced from carbon fiber. The spring plate had the following characteristics, as measured in connection with Formula I above:

TABLE 2

Spring Plate Characteristics

| Symbol | Definition | Value (in) | Value (mm) |
|--------|-----------|------------|------------|
| h | Thickness of spring | 0.06 | 1.5 |
| w | Width of spring | 2.75 | 70 |
| L | Distance between pivots | 1.57 | 40 |
| δ | Deflection | 0.395 | 10 |
| E | Tensile Modulus | 6.00E+06 (41 Gpa) | |
| F | Force exerted on/by heel | | |

The force exerted on/by this spring plate in order to advance it to the deflected position was 90.94 lbs.

Example 2

A cradle as illustrated in FIG. 8 was produced for use in applications in which there may be a risk of shoe puncture. The cradle was formed from 10 layers of 12 k carbon fiber woven by Sigmatex, (Benicia, Calif.) using Toray 700 fibers (Torray International America Inc., New York, N.Y.), and Resin Services Inc. (Sterling Heights, Mich.) epoxy resin. The layers forming the cradle were placed in a vacuum bag/autoclave @ 4 bar following curing for 2 hours at 200° F. The resulting cradles were 7 mm thick.

Example 3

A cradle was made using the method described in Example 2 above, except that 6 layers of the carbon fiber and one layer of KEVLAR were used, resulting in a cradle 5.6 mm thick. Beginning from the bottom side of the cradle, 1 layer of 12K carbon fiber was used, 6 layers of KEVLAR were then applied, and then a further layer of 12K carbon fiber was applied.

Example 4

A cradle was made using the method described in Example 2 above, except that 4 layers of KEVLAR and 7 layers of carbon fiber were used. Beginning from the bottom side of the cradle, 1 layer of 12K carbon fiber was used, 4 layers of KEVLAR were applied, and then a further 6 layer of 12K carbon fiber were applied.

Example 5

A spring plate was formed from a top layer and bottom layer of 12 k carbon fiber woven by Sigmatex, (Benicia, Calif.) using Toray 700 fibers (Torray International America Inc., New York, N.Y.) with 4 layers of Hexcel 7781 fiberglass fibers (Hexcel Corporation, San Clemente, Calif.) in between, bonded with PROSET epoxy resin (ProSet Inc., Bay City, Mich.). The spring plate was cured in a vacuum bag/autoclave at 27 inches Hg (0.914 bar) by ramping up the temperature to at 180° F. over the course of 3 hours, followed by 6 hours of curing at 180° F.

Example 6

A series of shoes and boots were tested for their puncture resistance and swing weight. Puncture protection was evaluated according to ASTM Standard F 2412-05 (Standard Test Methods for Foot Protection, as approved Mar. 1, 2005, published March 2005). Dynamic swing weight (moment of inertia) is an object's resistance to angular acceleration, and is calculated according to the following formula (Formula IV): $F = m \times v^2 / r$, where:

F is the swing weight (in Newtons);
m is the mass of the object in motion;
v is the tangential velocity; and
r is the distance of the object to the center of rotation.

Footwear was tested using a distance (r) of 1 meter and a tangential velocity of 5.55 meters per second. The results are shown in FIG. 16 and in Table 2 below. Figure legends in FIG. 16 are as follows:

A: CROCS sandals;
B: Nike SHOX athletic shoes;
C: BOXER (Israeli military) boots;
D: DANNER combat hiker boots;
E: BELLEVILLE boots;
F: RHINO wrestling shoe made according to Example 2 with 5 layers of 12K carbon fiber (Test Shoe A);
G: RHINO wrestling shoe made according to Example 2 with 8 layers of 12K carbon fiber and one layer of KEVLAR fiber (Test Shoe B); and
H: RHINO wrestling shoe containing a conventional 18 gage steel insert.

TABLE 3

Dynamic Swing Weight vs. Puncture Protection

| SAMPLE-ORTHOTIC AND SHOE | MASS (g) | DYNAMIC SWING WEIGHT* (N) | PUNCTURE PROTECTION (psi) |
|---|---|---|---|
| CROCS | 127 | 3912 | 24323 |
| NIKE SHOX | 409 | 12597 | 21742 |
| LIGHT COMBAT BOOT-BOXER ISRAEL | 533 | 16416 | 44839 |
| DANNER COMBAT HIKER | 891 | 27443 | 135355 |
| LIGHT COMBAT BOOT-BELLEVILLE | 975 | 30030 | 97484 |
| Test Shoe A | 510 | 15708 | 458194 |
| Test Shoe B | 560 | 17248 | 465097 |
| SIMPSON STRONG TIE 18 GAGE STEEL WITH RHINO WRESTLING SHOE | 441 | 13583 | 267613 |

A lower dynamic swing weight means that the object is easier to move or accelerate. As can be seen graphically in FIG. 16, shoes including the present spring orthotic device can provide superior puncture protection at a low swing weight, and thus a dramatically enhanced puncture protection at a given amount of footwear swing weight.

Example 7

Spring orthotics similar to those used in Example 6 with 10 mm thick carbon fiber cradles incorporating KEVLAR were incorporated into footwear for evaluation for their effect on jumping performance. Individuals performed a series of vertical jumps and standing broad jumps using RHINO wrestling shoes incorporating such spring orthotics, and the same individuals performed the same vertical jumps and standing broad jumps barefoot and with Nike SHOX athletic shoes and Belleville army boots.

The results of the vertical jump test are shown in FIG. 17, and the results of the standing broad jump test are shown in FIG. 18. Figure legends A-E in FIGS. 17 and 18 represent the following:

A: Barefoot
B: Nike SHOX athletic shoes
C: BELLEVILLE boots
D: RHINO wrestling shoe with 10 mm thick carbon fiber cradle with KEVLAR
E: Average The foregoing tests indicate that footwear incorporating the present spring orthotics having puncture-resistant cradles perform as well as or better than other footwear, and that the present spring orthotics do not decrease the performance of footwear.

Although the present invention has been discussed in considerable detail with reference to certain preferred embodiments, other embodiments are possible. The steps disclosed for the present methods are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A device for assisting locomotion using appendages, wherein the device comprises a proximal portion at a heel end of the device and a distal portion at a toe end of the device, comprising:

(a) a cradle having a proximal end, a distal end, an upper surface, and a lower surface, (b) a first planar spring plate positioned below the cradle and mechanically connected to the cradle, the spring plate having a proximal end, a distal end, a lateral side between the proximal end and the distal end, a medial side between the proximal end and the distal end, an upper surface, and a lower surface, wherein the proximal end of the cradle and the proximal end of the spring plate are separated by a vertical extent;

(c) a rigid ventral pivot positioned below the spring plate and mechanically connected to the spring plate, wherein the proximal end of the spring plate bends vertically downward around an axis defined by the length of the ventral pivot in response to a downward force applied to the proximal end of the cradle; and (d) a rigid dorsal pivot positioned between and mechanically connected to the cradle and to the spring plate, wherein the dorsal pivot is positioned proximally of the ventral pivot, wherein the ventral pivot is positioned between the lateral side and the medial side of the first planar spring plate distally of a point on the first planar spring plate which receives a ground reaction force during a first portion of a gait cycle.

2. The device of 1, wherein the dorsal pivot and ventral pivot comprise an outer surface having a cross-sectional shape selected from the group consisting of elliptical, hemispherical, tubular pivots, square, and contoured.

3. The device of claim 1, wherein the dorsal pivot and/or the ventral pivot are hollow.

4. The device of claim 1, wherein the cradle is configured to receive a human foot.

5. The device of claim 1, wherein the distal end of the cradle extends to a point above the first planar spring plate which is proximal to a point on the first planar spring plate which receives a ground reaction force during a second portion of the gait cycle, preferably adjacent to a point below the ball of a subject's foot.

6. The device of claim 1, further comprising rigid toe pivot attached to the lower surface of the first planar spring plate at a point located distally of the ventral pivot, wherein the toe pivot provides an axis around which the spring plate can bend downwardly during a toe-off portion of the gait cycle.

7. The device of claim 1, wherein the cradle is made from a material selected from the group consisting of carbon fiber, metal, ethylene vinyl acetate, nylon, polyethylene, polypropylene, polyurethane, carbon fiber, or fiberglass.

8. The device of claim 1, wherein the first planar spring plate is made from a material selected from the group consisting of carbon fiber, polycarbonate plastic, and steel, preferably carbon fiber including KEVLAR fiber and/or fiberglass.

9. The device of claim 1, wherein the spring plate comprises a plurality of materials, wherein each of the plurality of materials has a different property selected from the group consisting of spring coefficient, modulus of elasticity and tensile strength.

10. The device of claim 1, wherein the distal end of the first planar spring plate comprises a downwardly extending convex form.

11. The device of claim 1, further comprising a vertically extending support having a proximal end and a distal end, wherein the distal end is mechanically connected to the upper surface of the cradle, the vertically extending support comprising a mechanical appendage.

12. The device of claim 11, further comprising a handle attached to the proximal end of the vertically extending support, thereby forming a crutch.

13. The device of claim 11, further comprising a brace attached to the proximal end of the vertically extending support, wherein the brace extends horizontally and is designed to receive a portion of a subject's leg below the knee.

14. The device of claim 11, wherein the vertically extending support is attached at the distal end to a receptacle for an amputated limb, thereby forming a prosthetic.

15. The device of claim 11, wherein the distal end of the vertically extending support is mechanically connected to a mechanical device, the vertically extending support comprising a mechanical appendage for allowing the mechanical device to achieve locomotion.

16. The device of claim 1, further comprising:
a second planar spring plate positioned below the first planar spring plate, and
a second ventral pivot positioned below the second spring plate and mechanically connected to the second planar spring plate proximally of the ventral pivot positioned below the first planar spring plate.

17. The device of claim 1, further comprising a planar forefoot spring extending distally from the distal end of the first planar spring plate.

18. The device of claim 1, wherein the device is retained within a piece of footwear.

19. The device of claim 10, wherein the convex form of the distal end of the first planar spring plate is a hemispherical forefoot spring.

20. A device for assisting locomotion using appendages, wherein the device comprises a proximal portion at a heel end of the device and a distal portion at a toe end of the device, comprising:

(a) a cradle having a proximal end, a distal end, an upper surface, and a lower surface, (b) a first planar spring plate positioned below the cradle and mechanically connected to the cradle, the spring plate having a proximal end, a distal end, a lateral side between the proximal end and the distal end, a medial side between the proximal end and the distal end, an upper surface, and a lower surface, wherein the upper surface of the proximal end of the cradle and the upper surface of the proximal end of the spring plate are separated by a vertical extent;

(c) a rigid ventral pivot positioned below the spring plate and mechanically connected to the spring plate; and (d) a rigid dorsal pivot positioned between the cradle and the spring plate, wherein the dorsal pivot is positioned proximally of the ventral pivot, wherein the spring plate experiences a double bending during a first portion of a gait cycle, the spring plate bending vertically downward around the ventral pivot and vertically upward around the dorsal pivot in response to a downward force applied to the proximal end of the cradle.

21. The device of claim 20, wherein the dorsal heel pivot is within between 1 centimeter and 4 centimeters of the proximal end of the spring plate.

* * * * *